(12) United States Patent
Hamada et al.

(10) Patent No.: US 9,285,379 B2
(45) Date of Patent: Mar. 15, 2016

(54) INFORMATION MANAGEMENT APPARATUS AND SAMPLE TESTING APPARATUS THAT PERMIT FUNCTIONS BASED UPON OPERATOR ATTRIBUTES

(75) Inventors: Yuichi Hamada, Kobe (JP); Masaharu Shibata, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 479 days.

(21) Appl. No.: 12/845,165

(22) Filed: Jul. 28, 2010

(65) Prior Publication Data
US 2011/0039349 A1 Feb. 17, 2011

(30) Foreign Application Priority Data
Aug. 12, 2009 (JP) .................. 2009-187218

(51) Int. Cl.
*G01N 35/00* (2006.01)
*G01N 15/00* (2006.01)

(52) U.S. Cl.
CPC .... *G01N 35/00722* (2013.01); *G01N 35/00732* (2013.01); *G01N 35/00871* (2013.01); *G01N 2015/008* (2013.01); *G01N 2015/0073* (2013.01); *G01N 2015/0084* (2013.01); *G01N 2035/00891* (2013.01); *Y10T 436/25* (2015.01)

(58) Field of Classification Search
None
See application file for complete search history.

(56) References Cited

U.S. PATENT DOCUMENTS 6,544,476 B1 4/2003 Mimura et al.

FOREIGN PATENT DOCUMENTS

JP 2000-009735 A 1/2000
JP 2006-030100 A 2/2006

*Primary Examiner* — Yelena G Gakh
*Assistant Examiner* — Michelle Adams
(74) *Attorney, Agent, or Firm* — Brinks Gilson & Lione

(57) ABSTRACT

A sample testing apparatus comprising: a receiving section which receives identification information inputted by an operator; a testing section which tests a sample to obtain a test result; a memory which stores the test result, which is obtained by the testing section, so as to be associated with the identification information received by the receiving section; and a controller, wherein the controller is configured to: make a display section display only the test result associated with the identification information corresponding to a first attribute in the test results stored in the memory when the identification information received by the receiving section corresponds to the first attribute; and make the display section display test results which are stored in the memory when the identification information received by the receiving section corresponds to the second attribute is disclosed. An information management apparatus and sample testing method are also disclosed.

15 Claims, 20 Drawing Sheets

| ID | PASSWORD | GROUP |
|---|---|---|
| user1 | 1234 | GENERAL USER |
| user2 | 5678 | GENERAL USER |
| service1 | 9012 | SERVICEMAN |
| admin | 3456 | MANAGER |
| ⋮ | ⋮ | ⋮ |

FIG. 19

| ID | PASSWORD | GROUP |
|---|---|---|
| user1 | 1234 | GENERAL USER |
| user2 | 5678 | GENERAL USER |
| service1 | 9012 | SERVICEMAN |
| admin | 3456 | MANAGER |
| ⋮ | ⋮ | ⋮ |

FIG. 20

| SAMPLE ID | WBC | RBC | ⋯ | ID |
|---|---|---|---|---|
| 0001 | 4.8 | 4.0 | ⋯ | user1 |
| 0002 | 5.1 | 3.9 | ⋯ | user2 |
| 0003 | 3.8 | 5.0 | ⋯ | user2 |
| 1001 | 6.3 | 4.5 | ⋯ | service1 |
| ⋮ | ⋮ | ⋮ | ⋮ | ⋮ |

FIG. 21

| DATE | TIME | CONTENT | ID |
|---|---|---|---|
| 2009/5/1 | 13:02 | SAMPLING ERROR | user1 |
| 2009/5/2 | 14:34 | REPLACE PIERCER | user1 |
| 2009/5/2 | 15:28 | SAMPLING ERROR | user2 |
| 2009/5/3 | 17:35 | UNIT COVER IS OPEN | service1 |
| ... | ... | ... | ... |

INFORMATION MANAGEMENT APPARATUS AND SAMPLE TESTING APPARATUS THAT PERMIT FUNCTIONS BASED UPON OPERATOR ATTRIBUTES

RELATED APPLICATIONS

This application claims priority under 35 U.S.C. §119 to Japanese Patent Application No. 2009-187218 filed on Aug. 12, 2009, the entire content of which is hereby incorporated by reference.

FIELD OF THE INVENTION

The present invention relates to a sample testing apparatus for testing a sample obtained from a test subject, an information management apparatus and a sample testing method used in combination with the sample testing apparatus.

BACKGROUND

Japanese Laid-open Patent Publication No. 2006-030100 discloses a dispensing apparatus wherein any of three different levels of authorization, which are general user, manager, and serviceman, is preset to determine operator's identification information, the apparatus receiving the operator's ID inputted thereto and permitting the operator to carry out functions allowed for the authorization level corresponding to the inputted ID. It is further described in Japanese Laid-open Patent Publication No. 2006-030100 that the technique disclosed therein is applicable to analyzing apparatuses as well as dispensing apparatuses.

The dispensing apparatus permits the operator to execute functions allowed for general user when an ID having the general user's authorization level preset therein is inputted, permits the operator to execute functions allowed for manager and general user when an ID having the manager's authorization level preset therein is inputted, and permits the operator to execute functions allowed for manager, general user, and serviceman when an ID having the serviceman's authorization level preset therein is inputted. The operator, who is given the ID having the serviceman's authorization level preset therein, performs an operation check of the apparatus as a routine maintenance work to confirm whether or not the apparatus is normally operating based on an operation history thereby obtained.

The general user and the manager are operators who belong to a facility where the dispensing apparatus is installed. The serviceman is an operator who works for a vender who delivered the dispensing apparatus to the facility.

In a case where the technique described in Japanese Laid-open Patent Publication No. 2006-030100 is applied to an analyzing apparatus, the serviceman performs an analysis using a control specimen as a part of the maintenance work, and confirms whether or not the analyzing apparatus is normally operating by confirming an analysis result thus obtained. However, the analysis result of the control specimen thus generated by the maintenance work is unnecessary information for operators on the facility side. Therefore, the serviceman has to take an additional step of deleting the analysis result generated by the maintenance work after the maintenance is completed so that no operator on the facility side accesses the unnecessary information.

SUMMARY OF THE INVENTION

The scope of the present invention is defined solely by the appended claims, and is not affected to any degree by the statements within this summary.

A first aspect of the present invention is a sample testing apparatus comprising: a receiving section which receives identification information inputted by an operator; a testing section which tests a sample to obtain a test result; a memory which stores the test result, which is obtained by the testing section, so as to be associated with the identification information received by the receiving section; and a controller, wherein the controller is configured to: make a display section display only the test result associated with the identification information corresponding to a first attribute in the test results stored in the memory when the identification information received by the receiving section corresponds to the first attribute; and make the display section display the test result associated with the identification information corresponding to the first attribute and the test result associated with the identification information corresponding to a second attribute in the test results stored in the memory when the identification information received by the receiving section corresponds to the second attribute.

A second aspect of the present invention is a sample testing apparatus comprising: a testing section which tests a sample to obtain a test result; a memory which stores therein the test result obtained by the testing section so as to correspond to an attribute of an operator; a display section; and a controller, wherein the controller is configured to: making the display section display only the test result corresponding to a first attribute in the test results stored in the memory when the operator belongs to the first attribute; and making the display section display the test result corresponding to the first attribute and the test result corresponding to a second attribute when the operator belongs to the second attribute.

A third aspect of the present invention is an information management apparatus communicatably connected to a sample testing apparatus which tests a sample to obtain a test result, the information management apparatus comprising: a receiving section which receives identification information inputted by an operator; a memory which stores the test result, which is transmitted from the sample testing apparatus, so as to be associated with the identification information received by the receiving section; a display section; and a controller, wherein the controller is configured to: make the display section display only the test result corresponding to a first attribute in the test results stored in the memory when the identification information received by the receiving section corresponds to the first attribute; and make the display section display the test result corresponding to the first attribute and the test result corresponding to a second attribute in the test results stored in the memory when the identification information received by the receiving section corresponds to the second attribute.

A fourth aspect of the present invention is a sample testing method executed on a sample testing apparatus, the method comprising steps of: receiving identification information inputted by an operator; testing a sample to obtain a test result; associating the obtained test result with the received identification information and storing the resulting test result; outputting only the test result associated with the identification information corresponding to a first attribute in the stored test results when the received identification information corresponds to the first attribute; and outputting the test result associated with the identification information corresponding to the first attribute and the test result associated with the identification information corresponding to a second attribute in the stored test results when the received identification information corresponds to the second attribute.

BRIEF DESCRIPTION OF THE DRAWINGS

FIG. 19 is a schematic diagram illustrating an operator information database according to the embodiment of the present invention;

FIG. 20 is a schematic diagram illustrating a test result database according to the embodiment of the present invention; and FIG. 21 is a schematic diagram illustrating an operation history database according to the embodiment of the present invention.

DETAILED DESCRIPTION OF THE EMBODIMENT

A sample testing apparatus according to an embodiment of the present invention is a hemocyte analyzer which classifies and counts hemocyte components of a blood sample obtained from a test subject, such as red blood cells, white blood cells, and platelets.

Figure 1:
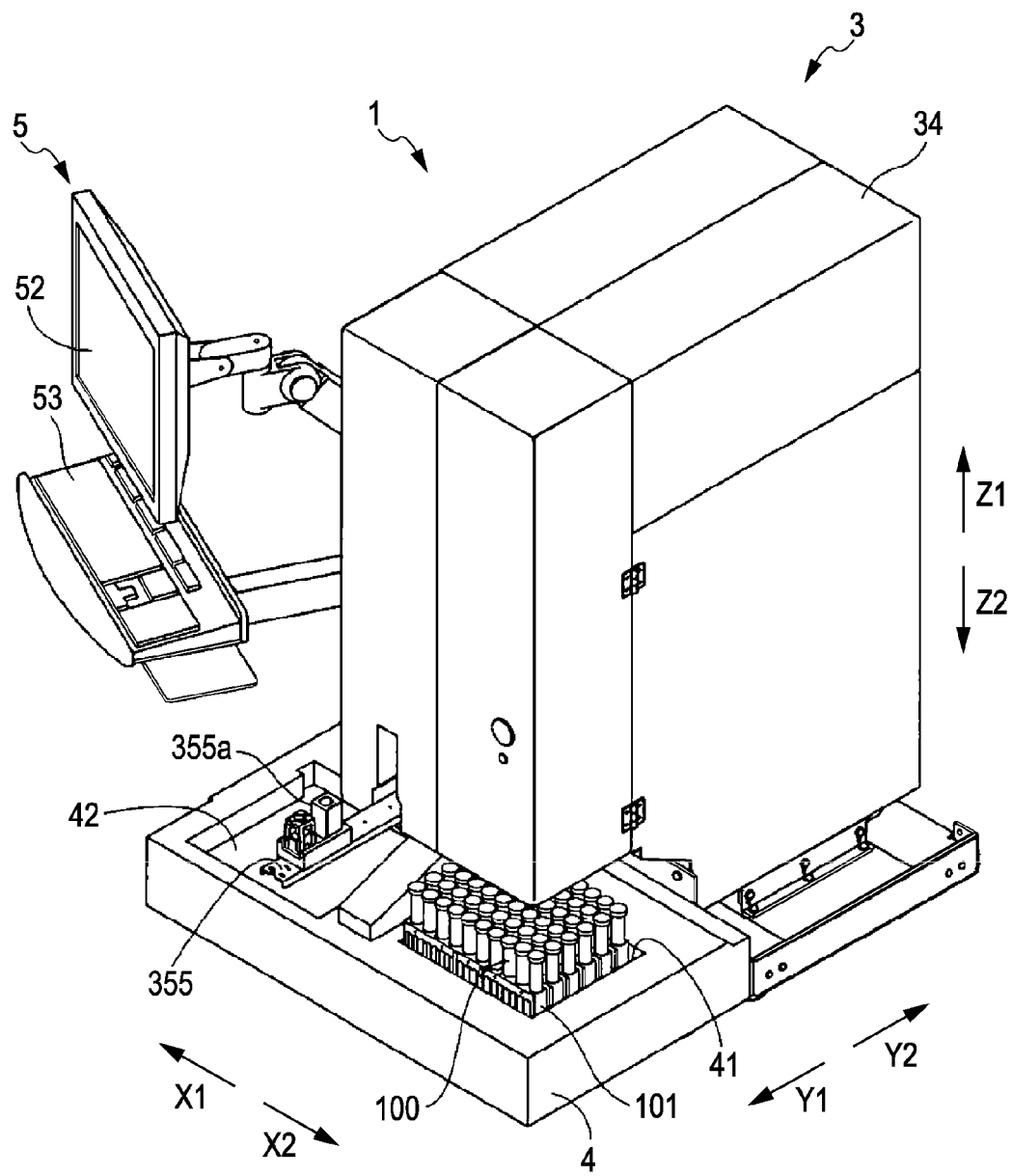
FIG. 1 is a perspective view illustrating external appearances and structures of a sample testing apparatus according to an embodiment of the present invention.

FIG. 1 is a perspective view illustrating external appearances and structures of a hemocyte analyzer 1. As illustrated in FIG. 1, the hemocyte analyzer 1 has a measurement unit 3, a conveying device 4 provided on a front-face side of the measurement unit 3 (on the side of an arrow-Y1 direction), and a controller 5 including a personal computer electrically connected to the measurement unit 3 and the conveying device 4. The controller 5 includes a display section 52 and an input device 53. The display section 52 is provided to display, for example, an analysis result obtained by analyzing data of digital signals transmitted from the measurement unit 3.

The conveying device 4 includes a pre-analysis rack holder 41 which can hold a plurality of racks 101 where sample containers 100 respectively containing pre-analysis samples are housed, a post-analysis rack holder 42 which can hold a plurality of racks 101 where sample containers 100 respectively containing post-analysis samples are housed, a rack conveying unit (not illustrated) which transversely conveys the racks 101 in directions of arrows X1 and X2, and a barcode reader (not illustrated) which reads a barcode 100b of each sample container 100 and also reads a barcode 101a attached to each rack 101.

Figure 2:
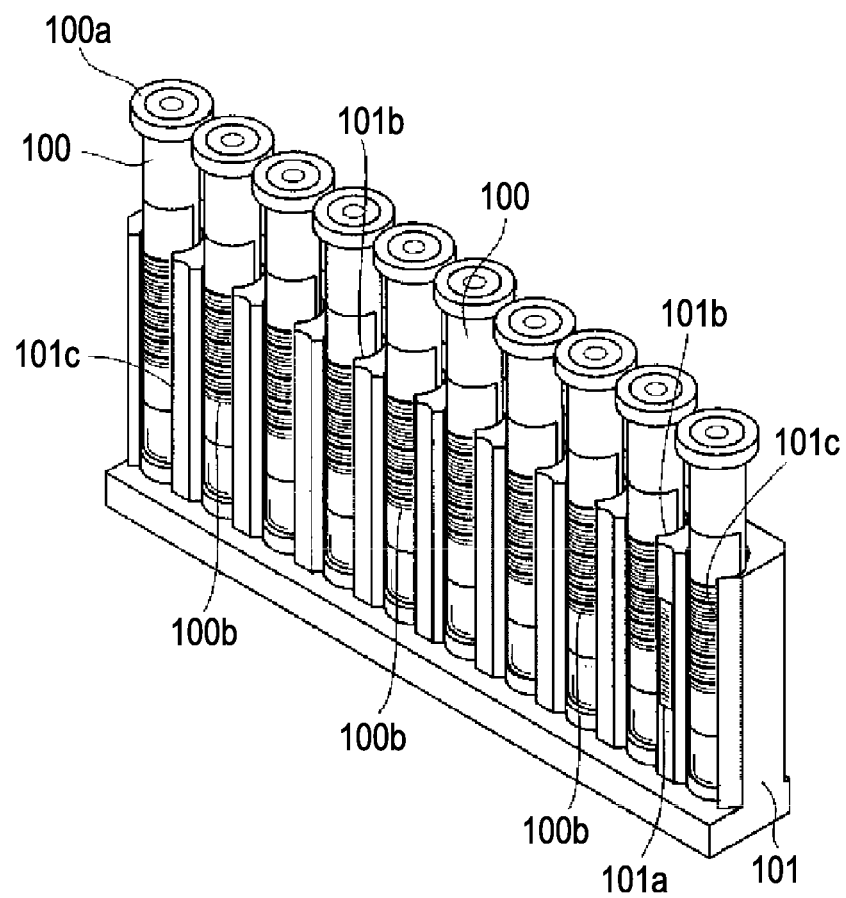
FIG. 2 is a perspective view illustrating external appearances and structures of a rack holding sample containers and the sample containers held in the rack.

FIG. 2 is a perspective view illustrating external appearances and structures of a rack holding the sample containers and the sample containers held in the rack. As illustrated in FIG. 2, ten container housing portions 101b are formed in the rack 101 to house therein ten sample containers 100 in an aligned manner. The barcodes 100b of the sample containers 100 are respectively uniquely attached to different samples so that they can be used to manage test results of the samples. The container housing portions 101b are each provided with an opening 101c so that the barcode 100b of the sample container 100 housed therein can be visually confirmed. The barcodes 101a of the racks 101 are each uniquely attached to each rack to manage the test results of the samples.

Figure 3:
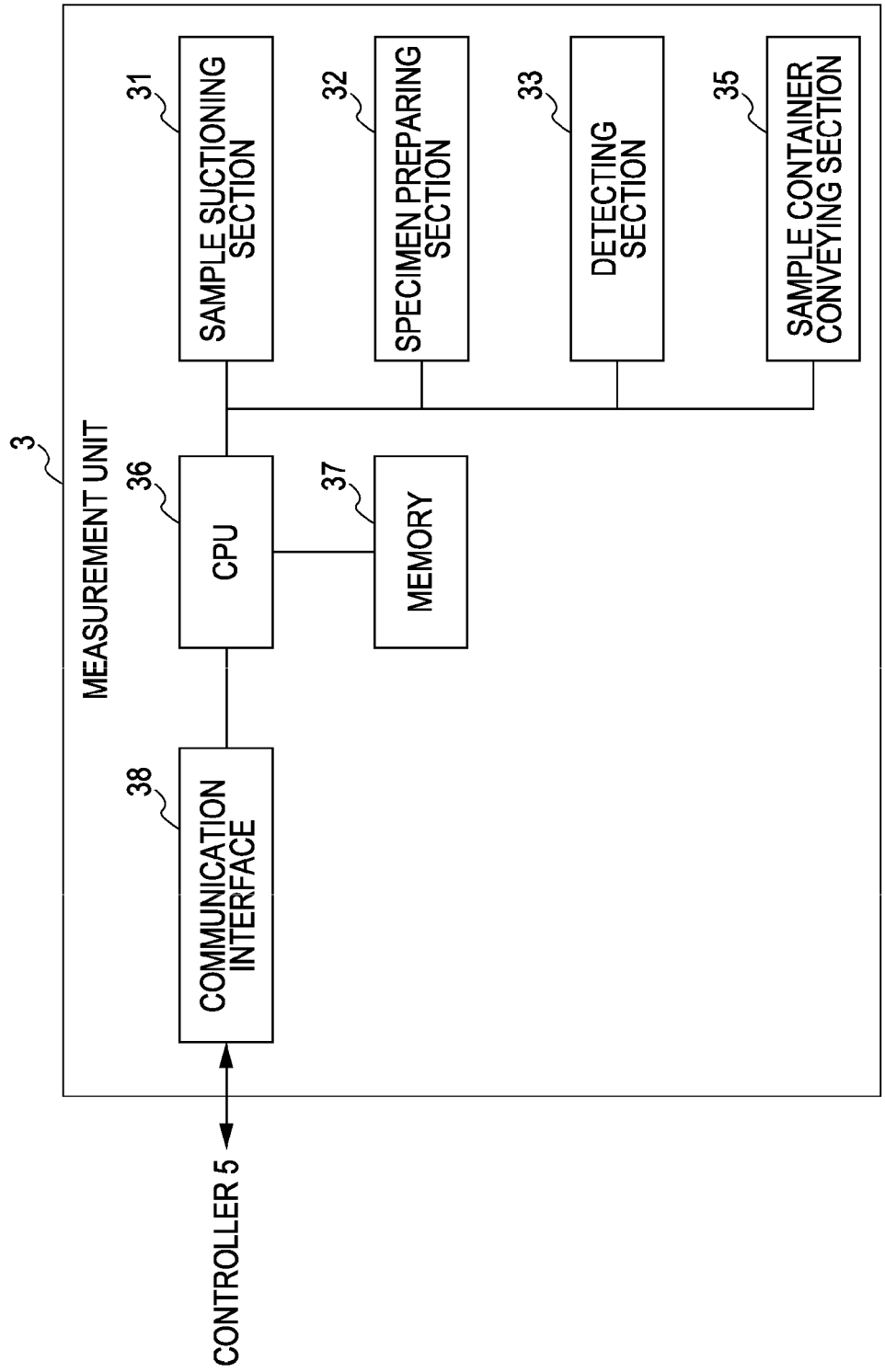
FIG. 3 is a block diagram illustrating a structure of a measurement unit according to the embodiment of the present invention.

FIG. 3 is a block diagram illustrating a structure of the measurement unit 3 provided in the hemocyte analyzer 1. As illustrated in FIG. 3, the measurement unit 3 includes a sample suctioning section 31 which suctions blood, which is a sample, from the sample container 100, a specimen preparing section 32 which prepares a specimen for detection from the blood suctioned by the sample suctioning section 31, and a detecting section 33 which detects blood hemocyte in the specimen for detection prepared by the specimen preparing unit 32. The measurement unit 3 further includes a unit cover 34 in which the sample suctioning section 31, the specimen preparing section 32, and the like are housed, and a sample container conveying section 35 which takes the sample container 100 into the unit cover 34 (see FIG. 1) and conveys the sample container 100 to a suctioning position by the sample suctioning section 31. The measurement unit 3 further includes a CPU 36 which controls the respective units, programs executed by the CPU 36, a memory 37 where data used to execute the programs is stored, and a communication interface 38 connected to the controller 5 to enable mutual communication therebetween.

The detecting section 33 detects RBC (red blood cells) and PLT (platelets) by means of sheath flow DC detection, and also detects HGB (hemoglobin in blood) by means of SLS-hemoglobin detection. The detecting section 33 also detects WBC (white blood cells) by means of flow cytometry in which semiconductor laser is used. The detection results obtained by the detecting section 33 are transmitted to the controller 5 as measurement data of the sample.

The sample container conveying section 35 has a hand portion (not illustrated) used to grasp the sample containers 100, a barcode reader (not illustrated), and a sample container conveying portion 355 which conveys the sample containers 100 in directions of arrows Y1 and Y2. The hand portion is provided at a position on the upper side of a conveyance path where the racks 101 are conveyed by the conveying device 4. The sample container conveying portion 355 has a sample setting part 355a (see FIG. 1), and can locate the sample setting part 355a at the suctioning position (not illustrated).

Figure 4:
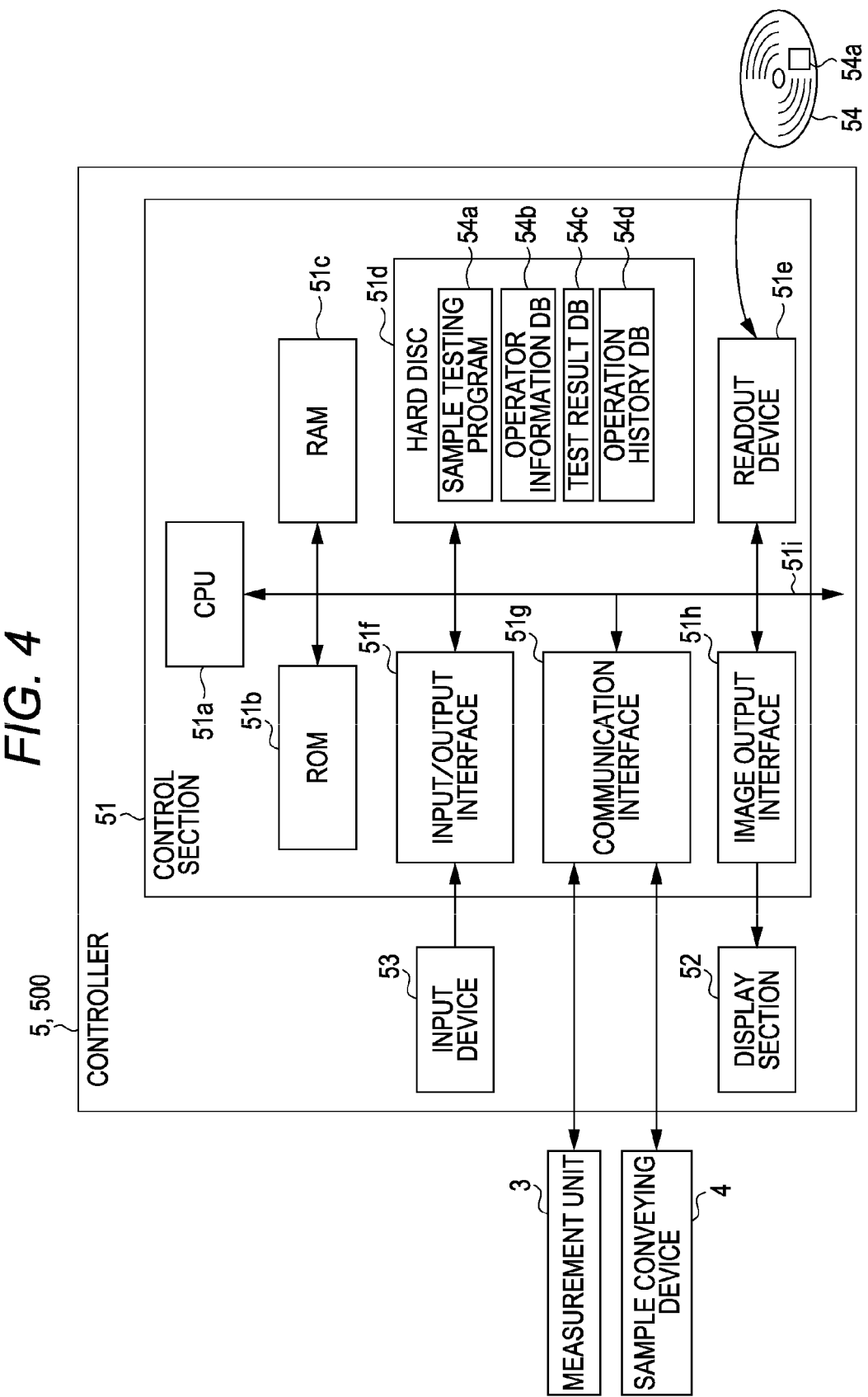
FIG. 4 is a block diagram illustrating a structure of a controller according to the embodiment of the present invention.

FIG. 4 is a block diagram illustrating a structure of the controller 5 of the hemocyte analyzer 1. As illustrated in FIG. 4, the controller 5 includes a computer 500 mainly having a control section 51, a display section 52, and an input device 53.

As illustrated in FIG. 4, the control section 51 mainly has a CPU 51a, a ROM 51b, a RAM 51c, a hard disc 51d, a readout device 51e, an input/output interface 51f, a communication interface 51g, and an image output interface 51h. The CPU 51a, ROM 51b, RAM 51c, hard disc 51d, readout device 51e, input/output interface 51f, communication interface 51g, and image output interface 51h are connected to one another by a bus 51i.

The CPU 51a is configured to execute a computer program stored in the ROM 51b and a computer program loaded in the RAM 51c. When an application program 54a, which will be described below, is executed by the CPU 51a, the computer 500 is able to function as the controller 5.

The ROM 51b includes a mask ROM, PROM, EPROM, EEPROM, or the like. The computer programs executed by the CPU 51a and any data used in the programs are recorded in the ROM 51b.

The RAM 51c includes an SRAM, DRAM, or the like. The RAM 51c is used to readout the computer programs recorded in the ROM 51b and the hard disc 51d. The RAM 51c is further used as a working region of the CPU 51a when these computer programs are executed.

In the hard disc 51d, there are installed various computer programs to be executed by the CPU 51a such as an operating system and application programs, and data used to execute the computer programs. The sample testing program 54a used by the controller 5 is also installed in the hard disc 51d. The hard disc 51d is further provided with an operator information database 54b, a test result database 54c, and an operation history database 54d. Each of the databases will be described in detail below.

The readout device 51e includes a flexible drive, a CD-ROM drive, or a DVD-ROM drive, and is configured to readout computer programs and data recorded on a portable recording medium 54. The application program 54a is stored in the portable recording medium 54. The computer 500 can readout the application program 54a from the portable recording medium 54 and install the application program 54a in the hard disc 51d.

It should be noted that not only the application program 54a can be provided from the portable recording medium 54, but also can be provided from an external apparatus connected to the computer 500 by an electric communication line (wired or wireless) to communicate therewith through the electric communication line. For example, the application program 54a may be stored in a hard disc of a server computer on the Internet, so that the computer 500 accesses the server computer to download the application program 54a and installs the downloaded program in the hard disc 51d.

In the hard disc 51d, there is installed, for example, an operating system which provides a graphical user interface environment, such as Windows (registered trademark) manufactured and sold by Microsoft Corporation, US. In the description given below, the application program 54a is executed on the above operating system.

The input/output interface 51f includes, for example, a serial interface such as USB, IEEE1394 or RS-232C, a parallel interface such as SCSI, IDE, or IEEE1284, or an analog interface including a D/A converter or an A/D converter. The input device 53 is connected to the input/output interface 51f. The operator can input data to the computer 500 by manipulating the input device 53.

An example of the communication interface 51g is an Ethernet (registered trademark) interface. Through the communication interface 51g, the computer 500 can transmit and receive data to and from the measurement unit 3 and the conveying device 4 using a predefined communication protocol.

The image output interface 51h is connected to the display section 52, examples of which are LCD and CRT, to output video signals corresponding to image data supplied from the CPU 51a to the display section 52. The display section 52 displays an image (screen) based on the video signals inputted thereto.

Figure 5:
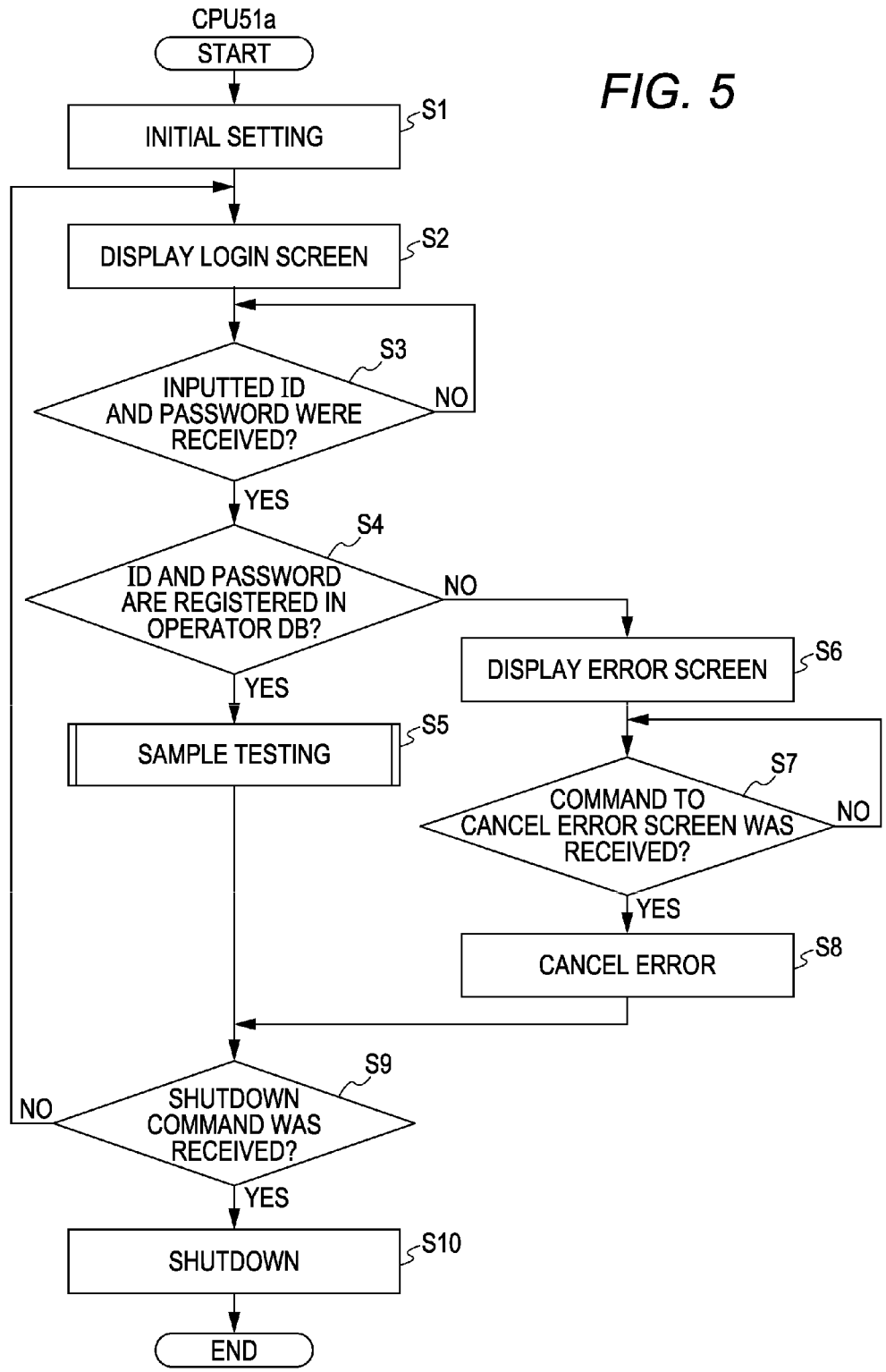
FIG. 5 is a flow chart illustrating a sample testing process of the controller according to the embodiment of the present invention.

FIG. 5 is a flow chart illustrating a sample testing process controlled by the controller 5 of the hemocyte analyzer 1. Hereinafter, the sample testing process of the controller 5 (CPU 51a) according to the present embodiment will be described referring to FIG. 5.

First, the CPU 51a performs an initial setting (S1), and then makes the display section 52 display a login screen F (see FIG. 6) thereon (S2).

Figure 6:
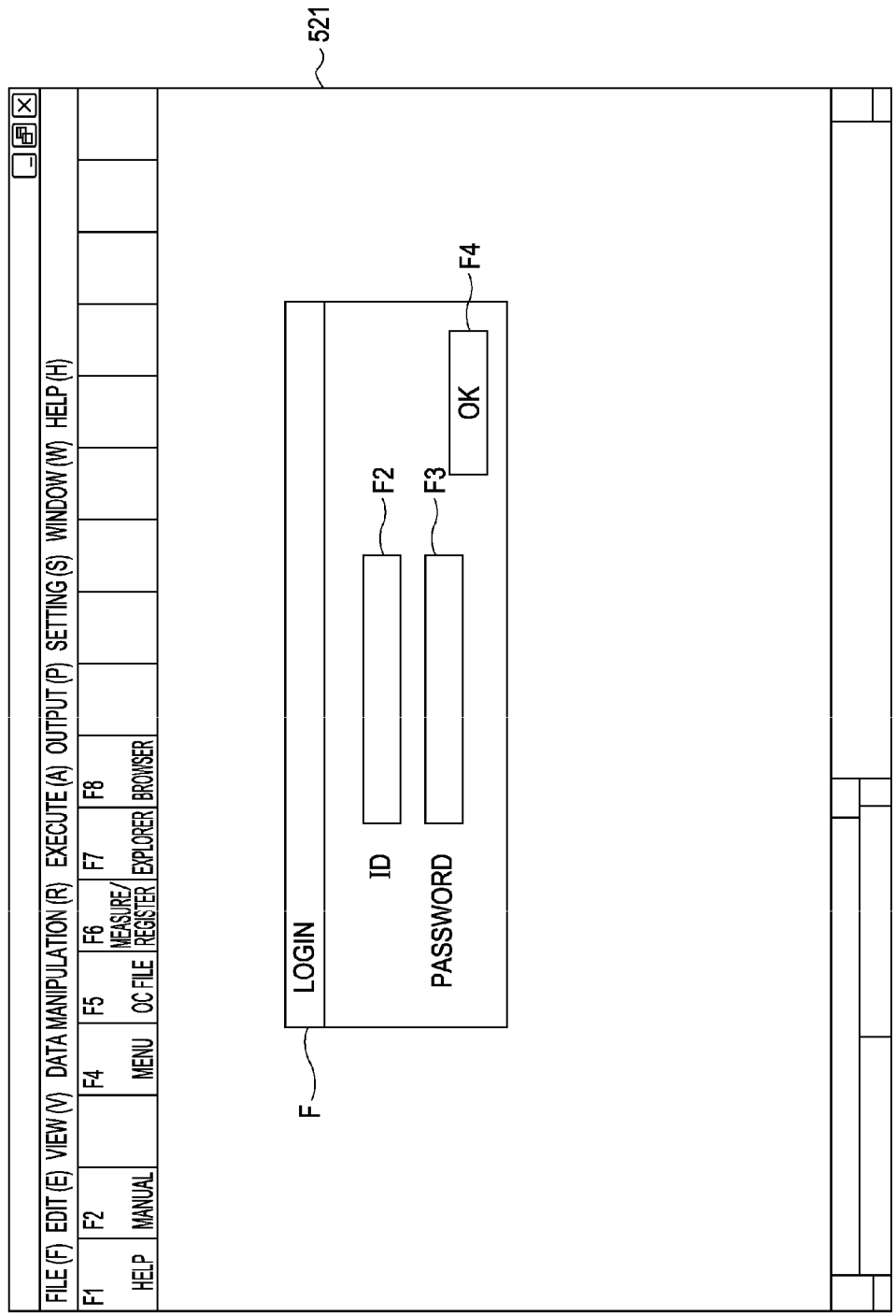
FIG. 6 is a diagram illustrating an example of a login screen according to the embodiment of the present invention.

FIG. 6 is a diagram illustrating an example of the login screen F displayed on the display section 52. As illustrated in FIG. 6, the login screen F has an ID field F2, a password field F3, and an OK button F4. The operator inputs an ID and a password to the ID field F2 and the password field F3 via the input device 53, and presses the OK button F4 to confirm the input of the ID and password. Herein, the ID is identification information for identifying the operator.

Returning to FIG. 5, the CPU 51a determines whether or not the inputted ID and password were received (S3). When it is determined that the inputted ID and password were received (S3: YES), the CPU 51a determines whether or not the received ID and the relevant password are registered in the operator information database 54b (S4).

FIG. 19 is a schematic diagram illustrating the operator information database 54b provided in the hard disc 51d. The operator information database 54b is a relational database, which has fields representing ID, password and group as illustrated in FIG. 19. The ID is information uniquely set for each operator, which is used to identify the operator. The password is a password arbitrarily set by the operator. The group represents information indicating which of three groups, general user, serviceman and manager, the operator belongs to. In the present embodiment, the operator is allowed to execute different functions depending on which of the groups the operator belongs to.

The operator who is a member of the general user group (hereinafter, referred to as general user) is an operator who works in a facility equipped with the hemocyte analyzer 1. One of the operator's duties is to test a sample obtained from a test subject. The general user's ID and password are registered in the operator information database 54b on a registration screen for general user (not illustrated) by the operator who belongs to the manager group (hereinafter, referred to as manager). Within the range set by the manager, the general user is able to perform various processes such as measuring the sample in the hemocyte analyzer 1, registering the measurement, modifying and deleting the test results, validating (approving) the test results, externally outputting the display screens, and changing settings.

The manager is an operator who belongs to the facility where the hemocyte analyzer 1 is installed. A main duty of the manager is the management of general users who access the hemocyte analyzer 1. The manager's ID and password are registered in the operator information database 54b by an operator who is a member of the serviceman group (hereinafter, referred to as serviceman). The manager can set for each general user which of the various functions of the hemocyte analyzer 1 can be carried out by the general user. The manager is authorized to carry out all of the functions of the hemocyte analyzer 1 that are allowed for the general user.

The serviceman is an operator working for a vender who delivers the hemocyte analyzer 1 to the facility. The serviceman is mainly in charge of a maintenance work of the hemocyte analyzer 1. The serviceman can, for example, change any settings which the general user and the manager are not allowed to change. The serviceman can, for example, set an error monitoring range of the analyzer and an error skip function in the analyzer, which are functions related to the maintenance work of the hemocyte analyzer 1. The serviceman is allowed to carry out all of the functions of the hemocyte analyzer 1 that are allowed for the general user, except modifying and deleting the test results and operation histories obtained by the general user.

Returning to FIG. 5, when it is determined that the inputted ID and the relevant password are registered in the operator information database 54b (S4: YES), the CPU 51a performs a sample testing operation (S5). The sample testing operation will be described in detail below.

When it is determined that the inputted ID and the relevant password are not registered in the operator information database 54b (S4: NO), the CPU 51a makes the display section 52 display an error screen J (see FIG. 7) thereon to notify that the inputted ID and password are not registered in the operator information database 54b (S6).

Figure 7:
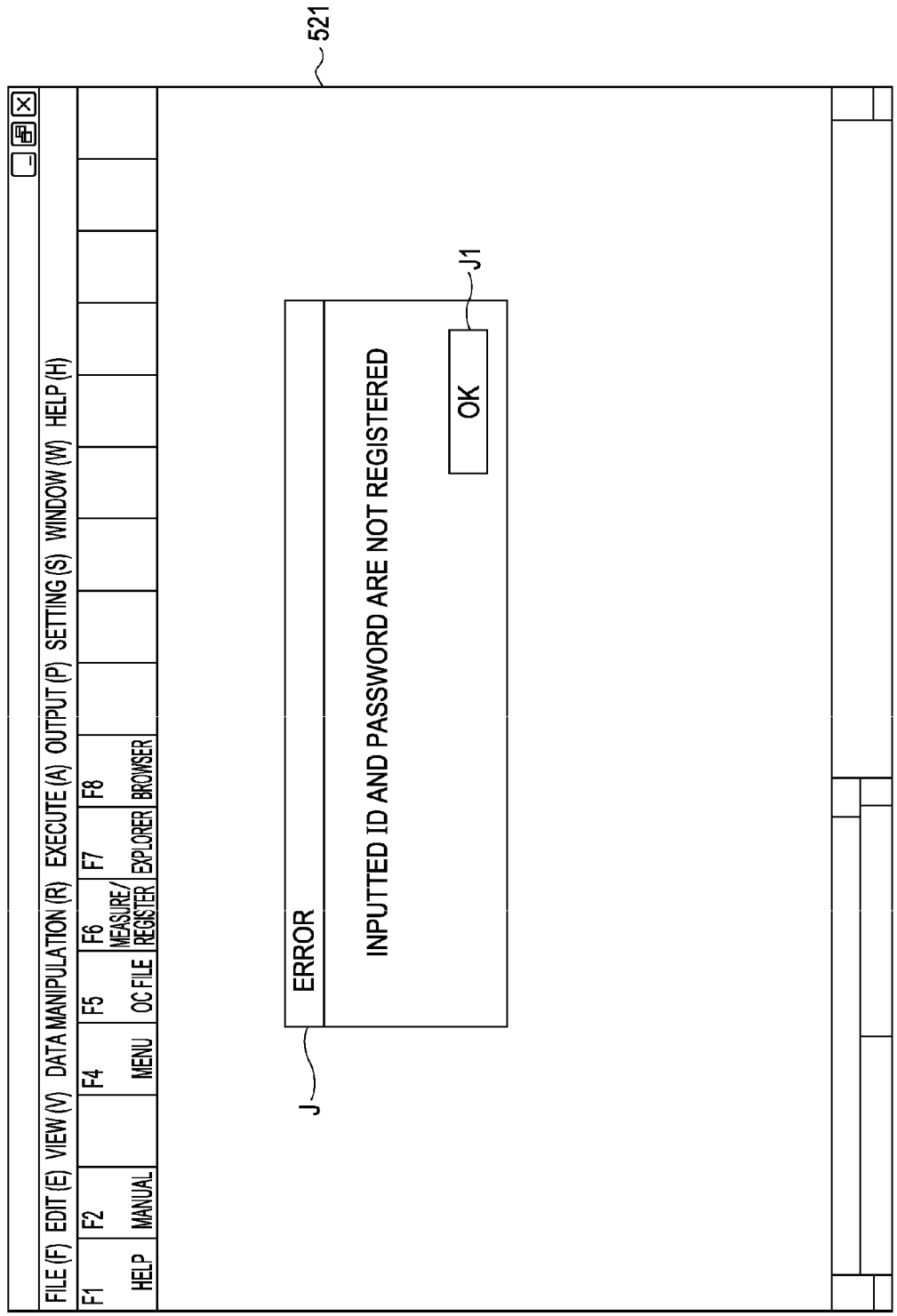
FIG. 7 is a diagram illustrating an example of an error screen according to the embodiment of the present invention.

FIG. 7 is a diagram illustrating an example of the error screen J displayed on the display section 52. As illustrated in FIG. 7, the error screen J displays a message, "the inputted ID and password are not registered". The error screen J also displays an OK button J1. The operator can command to cancel the error screen by selecting the OK button J1 via the input device 53.

Returning to FIG. 5, the CPU 51a determines whether or not a command to cancel the error screen was received (S7). When it is determined that the command to cancel the error screen was received (S7: YES), the CPU 51a performs an error cancel process to cancel the error screen J displayed on the display section 52 (S8).

Next, the CPU 51a determines whether or not a shutdown command from the operator was received (S9). When it is determined that the shutdown command was received (S9: YES), the CPU 51a performs a shutdown process (S10). When it is determined that the shutdown command was not received (S9: NO), the CPU 51a performs the process in step S2.

Figure 8:
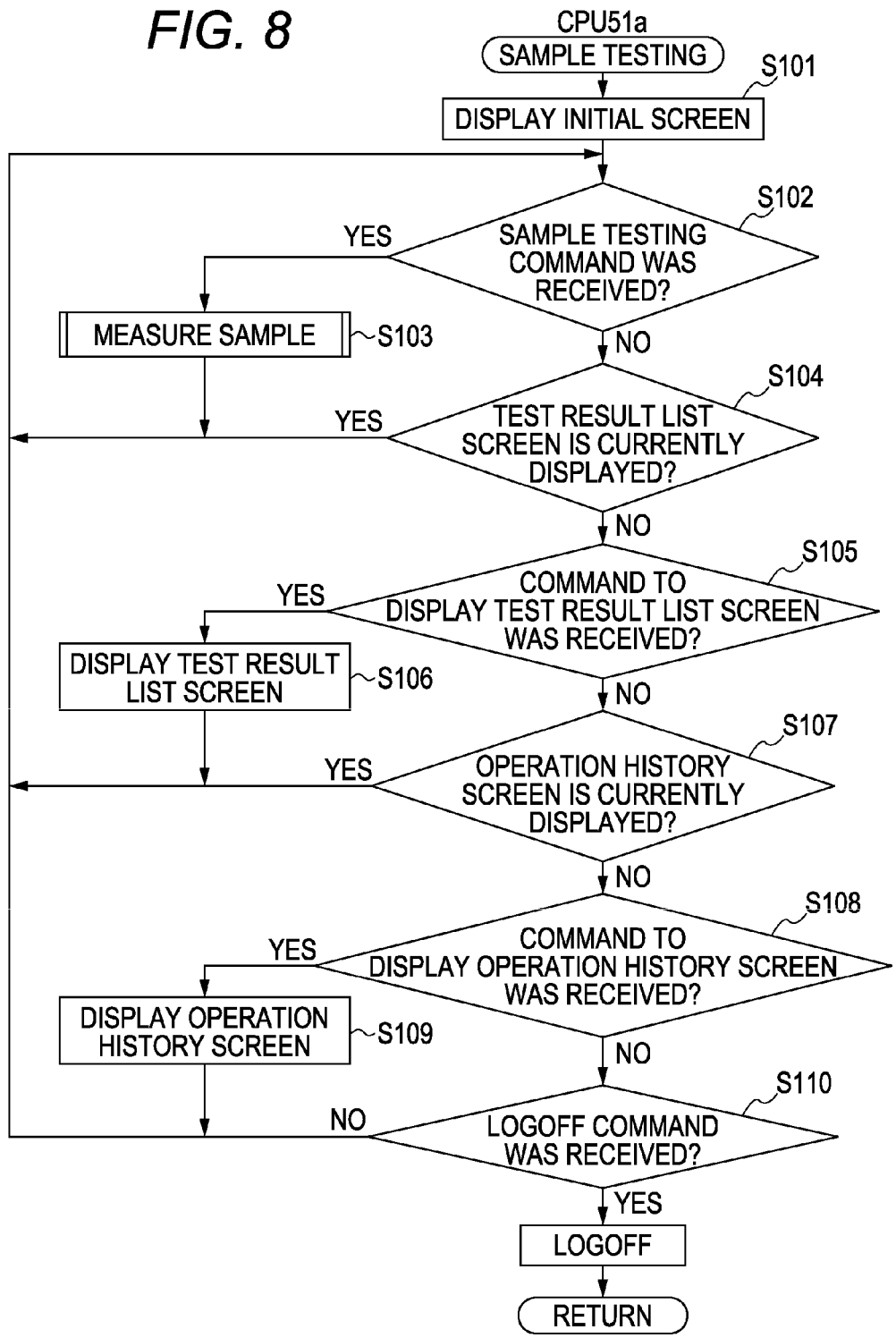
FIG. 8 is a flow chart illustrating a sample testing process according to the embodiment of the present invention.

FIG. 8 is a flow chart illustrating a sample testing process by the CPU 51a. Referring to FIG. 8, the sample testing process controlled by the controller (CPU 51a) will be described below. In the sample testing process, different screens are displayed on the display section 52 depending on whether step 3 determines that the general user's ID was inputted and received or the serviceman's ID was inputted and received. This point will be described below.

<When Operator is General User>

In the following, there will be described a sample testing process in a case where the general user's ID was inputted and received in step S3.

First, the CPU 51a makes the display section 52 display an initial screen 521 for general user (see FIG. 9) thereon (S101).

Figure 9:
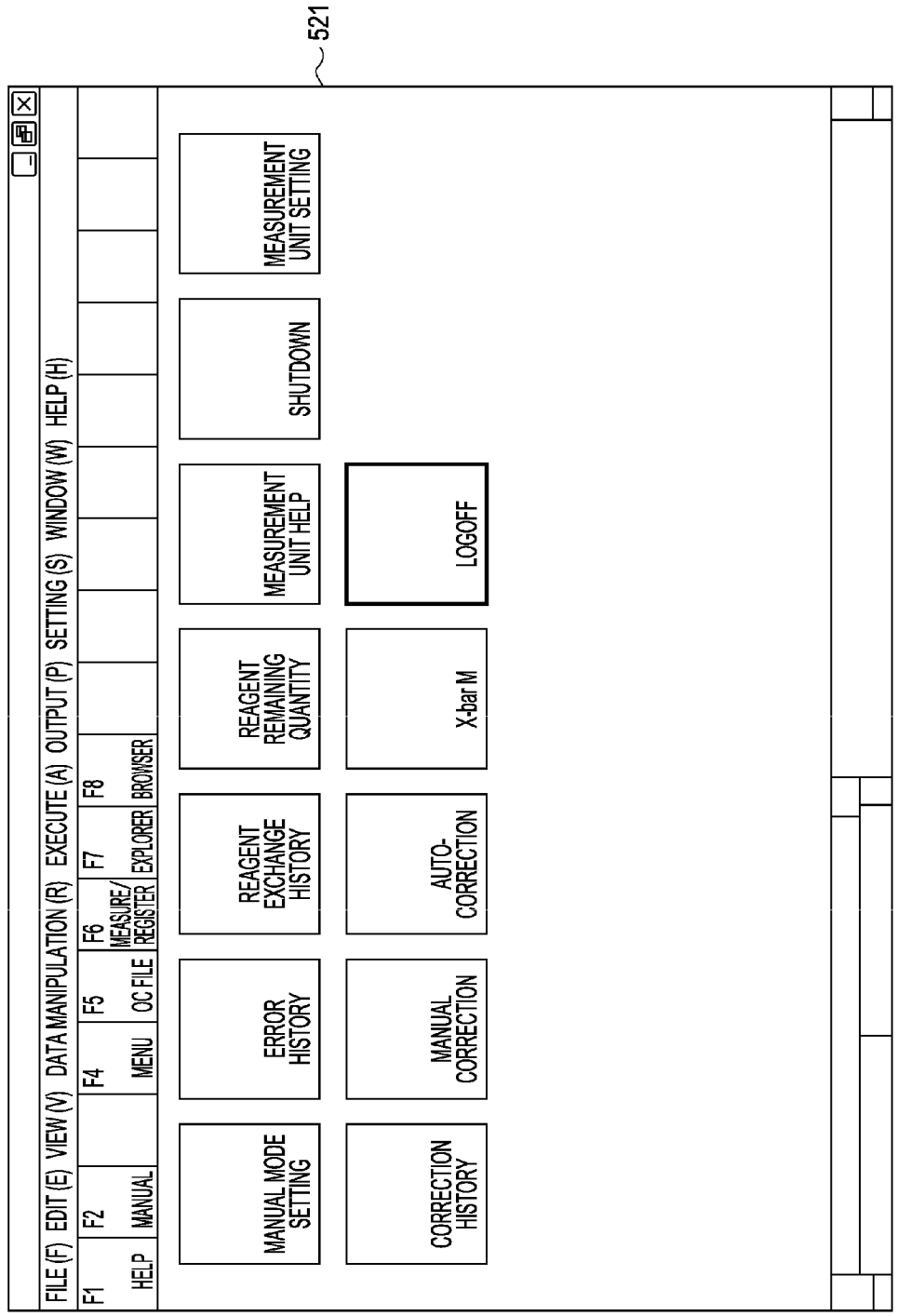
FIG. 9 is a diagram illustrating an example of an initial screen for general user according to the embodiment of the present invention.

FIG. 9 is a diagram illustrating an example of the initial screen 521 for general user displayed on the display section 52. As illustrated in FIG. 9, the initial screen 521 is equipped with various buttons displayed thereon which are used to command the CPU 51a to perform the processes, for example, sample measurement, setting screen display, test result display, operation history display, logoff, and shutdown. The operator can command the CPU 51a to selectively perform the respective processes by selecting to press any of the buttons via the input device 53.

Next, the CPU 51a determines whether or not the sample measurement command from the operator was received (S102). When it is determined that the sample measurement command was received (S102: YES), the CPU 51a performs a sample measuring process (S103).

Figure 10:
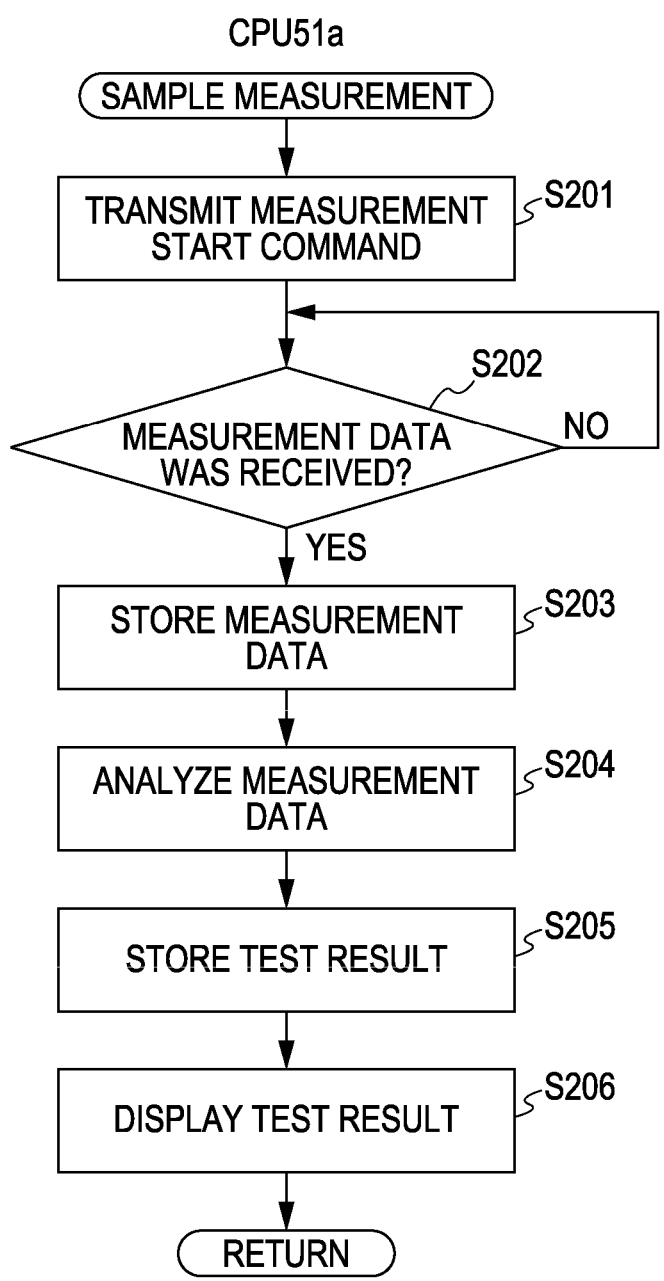
FIG. 10 is a flow chart illustrating a sample measuring process according to the embodiment of the present invention.

FIG. 10 is a flow chart illustrating a sample measuring process controlled by the controller 5 of the hemocyte analyzer 1. Referring to FIG. 10, the sample measuring process of the controller 5 (CPU 51a) will be described below.

First, the CPU 51a transmits a command to start the sample measurement to the measurement unit 3 (S201). The sample measuring operation by the measurement unit 3 will be described in detail below. Then, the CPU 51a determines whether or not the measurement data transmitted from the measurement unit 3 was received (S202). When it is determined that the inputted measurement data was received (S202: YES), the CPU 51a stores the received measurement data in the RAM 51c (S203). The CPU 51a analyzes the measurement data stored in the RAM 51c to acquire a test result (S204). The CPU 51a then associates the acquired test result with the operator's ID and stores the test result thus processed in the database 54c of the hard disc 51d (S205).

FIG. 20 is a schematic diagram illustrating the test result database 54c provided in the hard disc 51d. The test result database 54c will be described below referring to FIG. 20. The test result database 54c is a relational database, which includes fields each representing sample ID, date, time, WBC, RBC, . . . , ID. The sample ID is identification information uniquely defined for each of the samples housed in the sample containers 100. The date indicates year, month and day when the test result was obtained. The time indicates a time point when the test result was obtained. The WBC and RBC are test items, respectively representing the numbers of white blood cells and red blood cells in the blood. The test items are not necessarily limited to the WBC and RBC, and may be the number of platelets and an amount of hemoglobin. The ID indicates an ID of an operator who is operating the analyzer when the test result was obtained.

Returning to FIG. 10, the CPU 51a makes the display section 52 display thereon a test result display screen B (see FIG. 11) showing the test results stored in the test result database 54c (S206).

Figure 11:
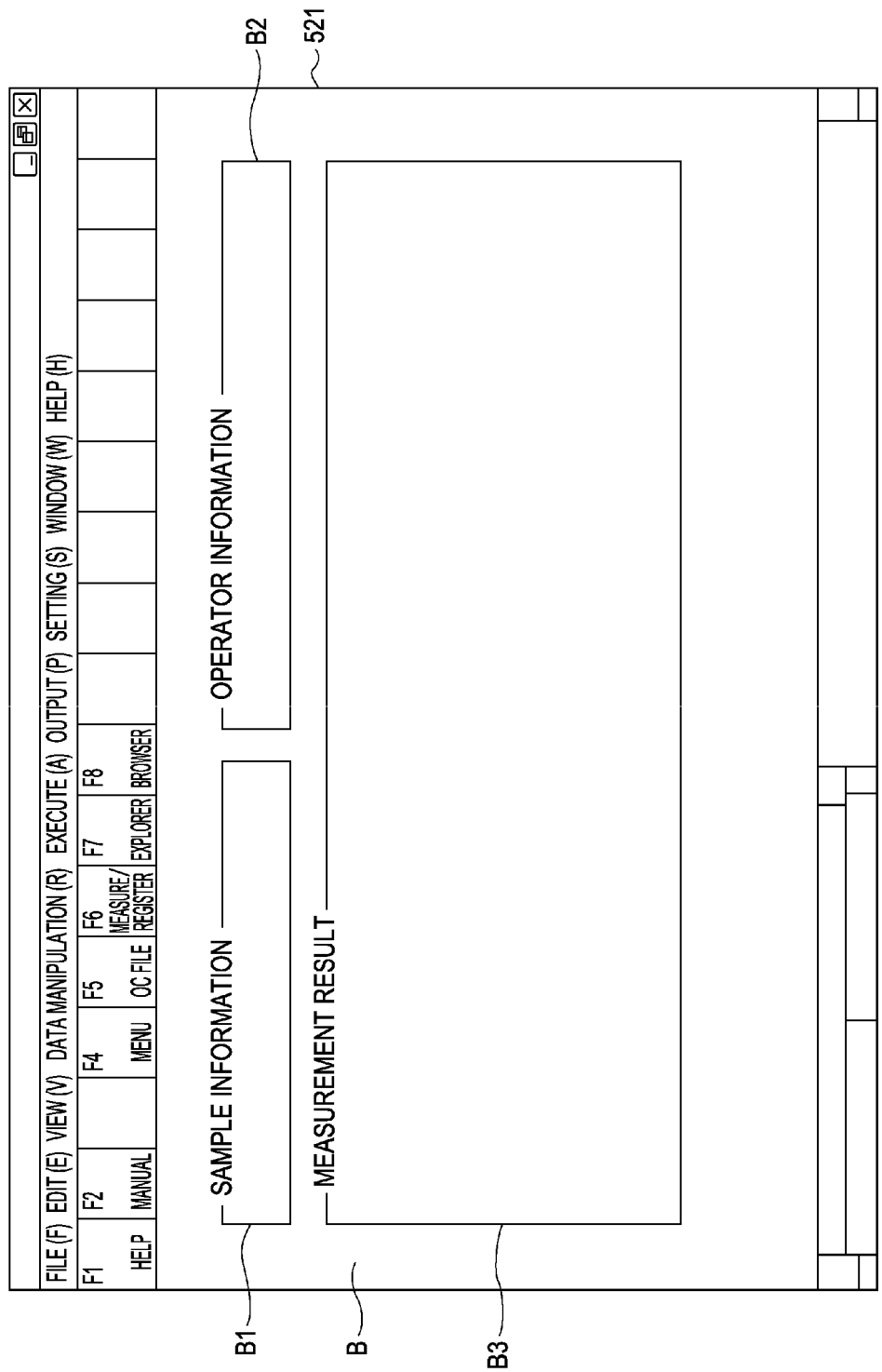
FIG. 11 is a diagram illustrating an example of a measurement result screen for general user according to the embodiment of the present invention.

FIG. 11 is a diagram illustrating an example of the measurement result display screen B displayed on the display section 52. As illustrated in FIG. 11, the test result display screen B includes a sample information field B1 where the sample ID or the like is displayed, an operator information field B2 where the ID of the operator who carried out the test, or the like, is displayed, and a measurement result field B3 where the test items of the sample are displayed. When a given period of time has passed after the test result display screen B was displayed on the display section 52, the CPU 51a performs the process in step S102 illustrated in the flow chart of FIG. 8.

Figure 12:
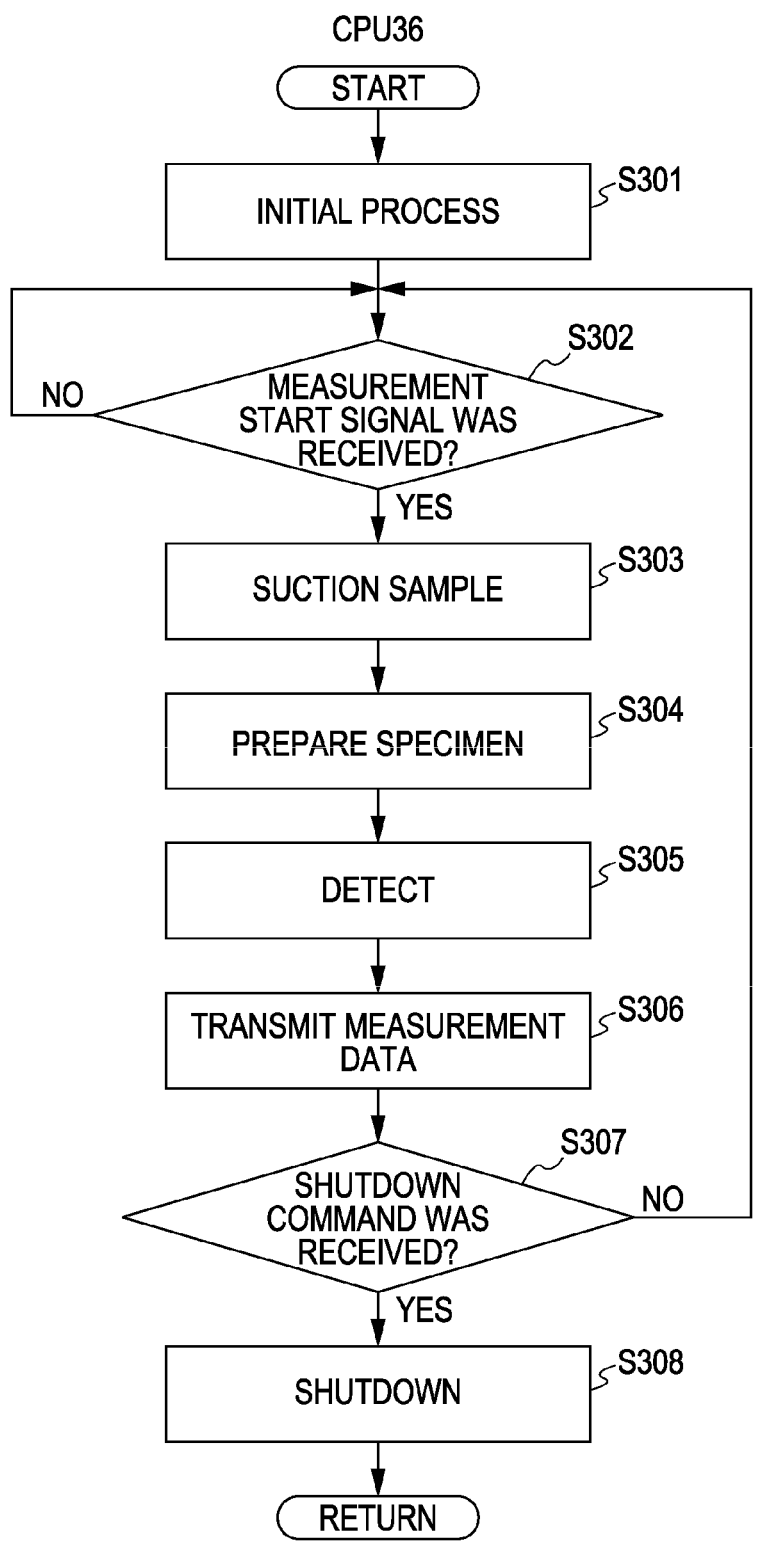
FIG. 12 is a flow chart illustrating a sample measuring operation carried out by the measurement unit according to the embodiment of the present invention.

FIG. 12 is a flow chart illustrating a sample measuring operation by the measurement unit 3 (CPU 36) according to the present embodiment. Referring to FIG. 12, the sample measuring operation by the measurement unit 3 (CPU 36) will be described below.

The CPU 36 performs an initial process such as returning each part of the measurement unit 3 to its initial operating position (S301). Next, the CPU 36 determines whether or not a command to initiate measurement transmitted from the controller 5 was received (S302). When it is determined that the sample measurement initiating command was received (S302: YES), the CPU 36 controls the sample suctioning section 31 so that the sample is suctioned from the sample container 100 conveyed to the suctioning position (S303), and controls the specimen preparing section 32 so that the specimen for detection is prepared from the suctioned sample (S304). The CPU 36 then controls the detecting section 33 so that the components to be analyzed are detected from the specimen for detection (S305), and transmits the obtained measurement data to the controller 5 (S306).

Then, the CPU 36 determines whether or not the shutdown command from the controller 5 was received (S307). When it is determined that the shutdown command was received (S307: YES), the CPU 36 transmits the operation history to the controller 5 and then performs the shutdown process (S308). When it is determined that the shutdown command was not received (S307: NO), the CPU 36 performs the process in step S302.

On the other hand, the CPU 51a receives the operation history transmitted from the measurement unit 3. Then, the CPU 51a associates the received operation history with the operator's ID and stores the operation history thus processed in the operation history database 54d provided in the hard disc 51d.

FIG. 21 is a schematic diagram of the operation history database 54d provided in the hard disc 51d. Referring to FIG. 21, the operation history database 54d will be described below. The operational history database 54d is a relational database, which includes fields each indicating date, time, content, and ID. The date indicates year, month and day when the operation history was created. The time indicates a point of time when the operation history was created. The content indicate the contents of the operation history (such as error). The ID is the ID of the operator who was operating the analyzer when the operation history was created.

Returning to FIG. 8, when it is determined that the sample measurement command was not received (S102: NO), the CPU 51a determines whether or not a test result list screen E (see FIG. 13) is currently displayed on the display section 52 (S104). When it is determined that the test result list screen E is not currently displayed on the display section 52 (S104: NO), the CPU 51a determines whether or not a command to display the test result list screen E was received (S105). When it is determined that the command to display the test result list screen E was received (S105: YES), the CPU 51a displays the test result list screen E on the display section 52 (S106).

Figure 13:
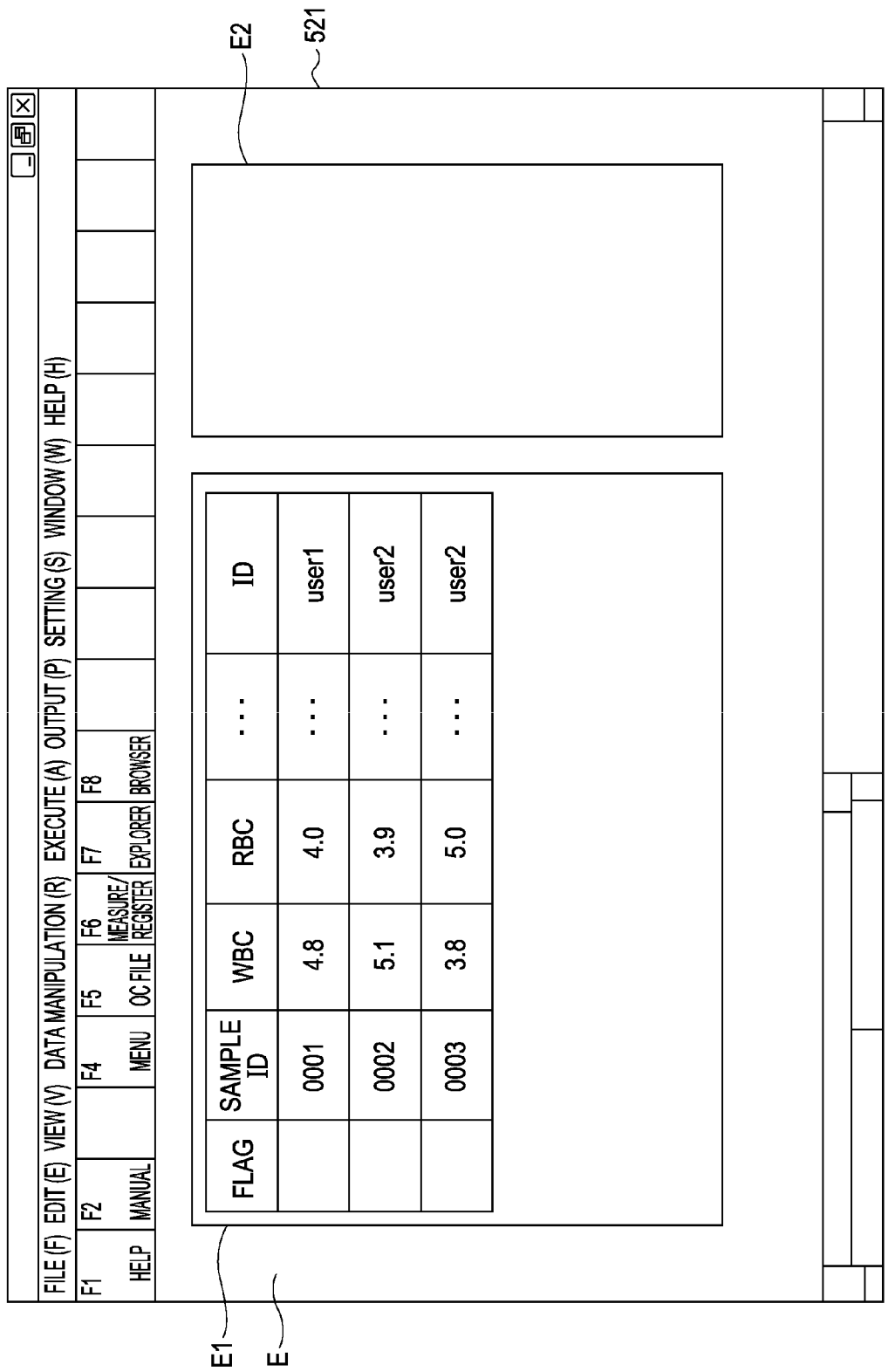
FIG. 13 is a diagram illustrating an example of a test result list screen for general user according to the embodiment of the present invention.

FIG. 13 is a diagram illustrating an example of the test result list screen E displayed on the display section 52. As illustrated in FIG. 13, the test result list screen E includes a summary display field E1 which displays the summarized test results, and a detail display field E2 which displays the details of the test results selected in the summary display field E1.

In a case where the logged-in operator is a general user, only the test results obtained by general users in all of the test results registered in the test result database 54c are selectively displayed on the test result list screen E, while the test results obtained by the serviceman are not displayed thereon. More specifically, only the test results associated with the general user's ID are displayed on the test result list screen E, while the test results associated with the serviceman's ID are not displayed on the test result list screen E. In this manner, the general user no longer needs to access the test results generated by the serviceman's maintenance work, which is unnecessary information for the general user.

Returning to FIG. 8, when it is determined that the test result list screen E is currently displayed on the display section 52 (S104: YES) or the CPU 51a newly commands to display the test result list screen E on the display section 52, the CPU 51a performs the process in step S102.

When it is determined that the command to display the test result list screen E was not received (S105: NO), the CPU 51a determines whether or not an operation history list screen G (see FIG. 14) is currently displayed on the display section 52 (S107). When it is determined that the operation history list screen G is not currently displayed on the display section 52 (S107: NO), the CPU 51a determines whether or not a command to display the operation history screen was received (S108). When it is determined that the command to display the operation history screen was received (S108: YES), the CPU 51a makes the display section 52 display the operation history list screen G thereon (S109).

Figure 14:
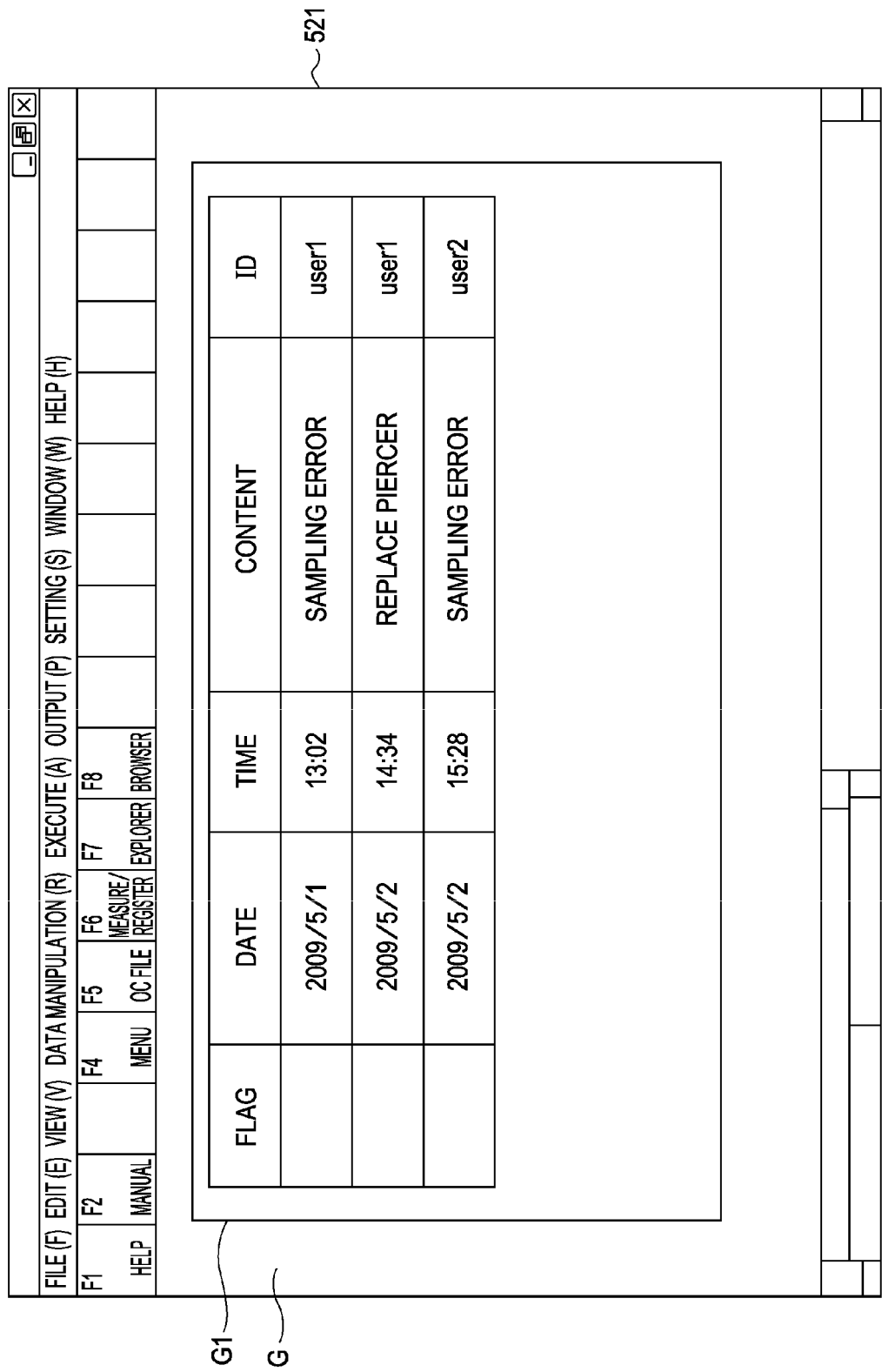
FIG. 14 is a diagram illustrating an example of an operation history list screen for general user according to the embodiment of the present invention.

FIG. 14 is a diagram illustrating an example of the operation history list screen G displayed on the display section 52. As illustrated in FIG. 14, the operation history list screen G includes an operation history list field G1 where an operation history list is displayed.

In a case where the logged-in operator is a general user, only the operation histories obtained by general users are selected from all of the operation histories registered in the operation history database 54d to be displayed on the operation history list screen G, while the operation histories obtained by the serviceman are not displayed. More specifically, only the operation histories associated with the general user's ID are displayed on the operation history list screen G, while the operation histories associated with the serviceman's ID are not displayed on the operation history list screen G. In this manner, the general user no longer needs to access the operation histories generated by the serviceman's maintenance work which is unnecessary information for the general user.

Returning to FIG. 8, when the operation history list screen G is currently displayed on the display section 52 (S107: YES) or the CPU 51a newly commands to display the operation history list screen G on the display section 52, the CPU 51a performs the process in step S102.

When it is deter mined that the command to display the operation history list screen G was not received (S108: NO), the CPU 51a determines whether or not a logoff command was received (S110). The CPU 51a performs a logoff process (S111) when it is determined that the logoff command was received (S110: YES), while the CPU 51a performs the process in step S102 when it is determined that the logoff command was not received (S110: NO).

Although the sample testing process in a case where the operator is a general user have been described above, the process similar to the above sample testing process may be carried out in a case where the operator is a manager.

<When Operator is Serviceman>

Referring to the flow chart illustrated in FIG. 8, a description will be given to the sample testing process in a case where the ID inputted by the serviceman was received in step S3 of the flow chart illustrated in FIG. 5.

First, the CPU 51a makes the display section 52 display an initial screen 521 for serviceman (see FIG. 15) thereon (S101).

Figure 15:
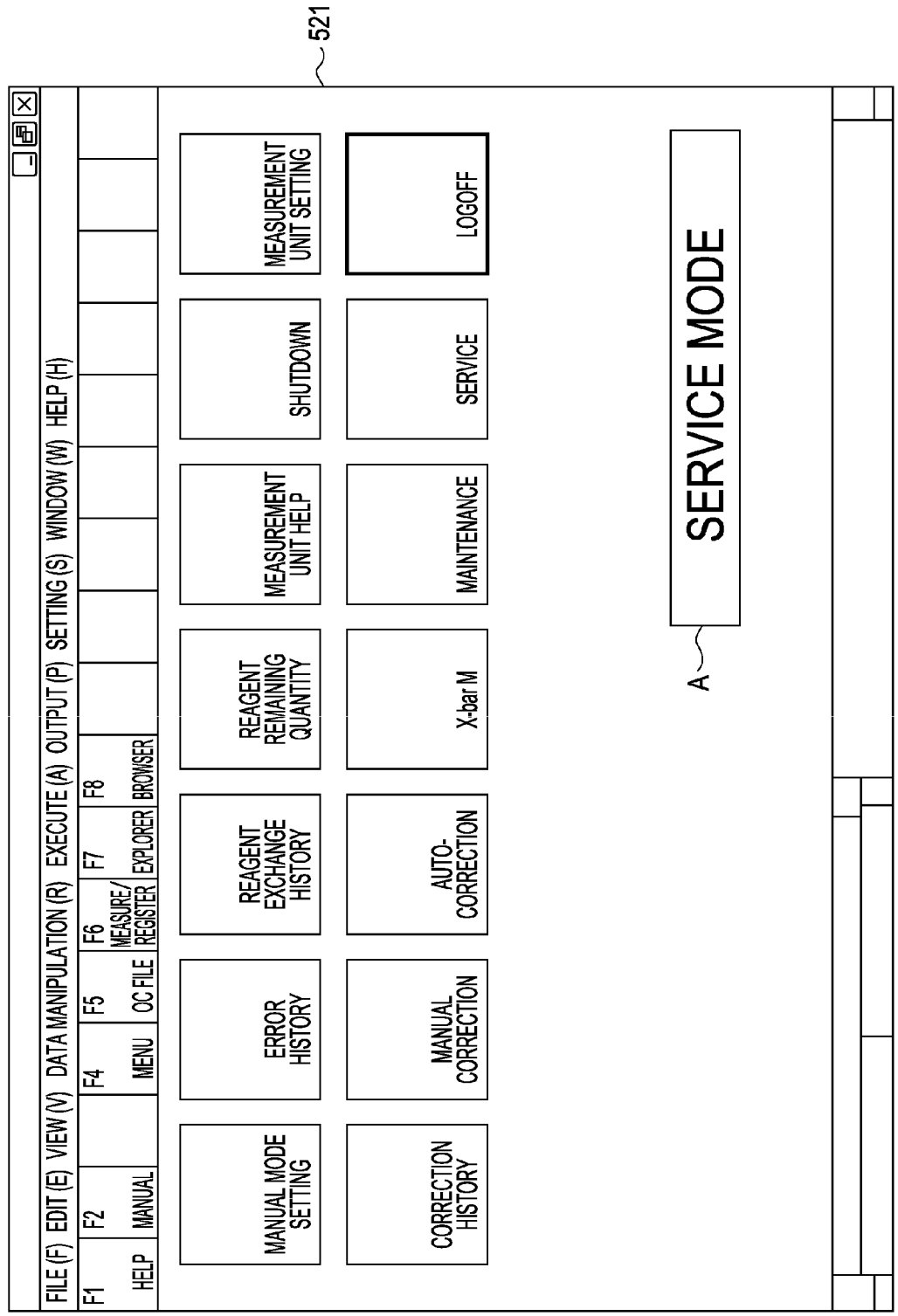
FIG. 15 is a diagram illustrating an example of an initial screen for serviceman according to the embodiment of the present invention.

FIG. 15 is a diagram illustrating an example of the initial screen 521 for serviceman displayed on the display section 52. All of the screens displayed on the display section 52 in the case where the operator is a serviceman, i.e., the initial screen 521 (see FIG. 15), measurement result display screen B (see FIG. 16), test result list screen E (see FIG. 17), and operation history list screen G (see FIG. 18) include a mode display bar A which indicates that the current operator is a serviceman.

Returning to FIG. 8, the CPU 51a determines whether or not the sample measurement command was received from the operator (S102). When it is determined that the sample measurement command was received (S102: YES), the CPU 51a performs the sample measurement process (S103). In such sample measurement, the serviceman measures a control specimen and confirms a measurement result thereby obtained and operation histories of the analyzer to check whether the hemocyte analyzer 1 is normally operating.

Figure 16:
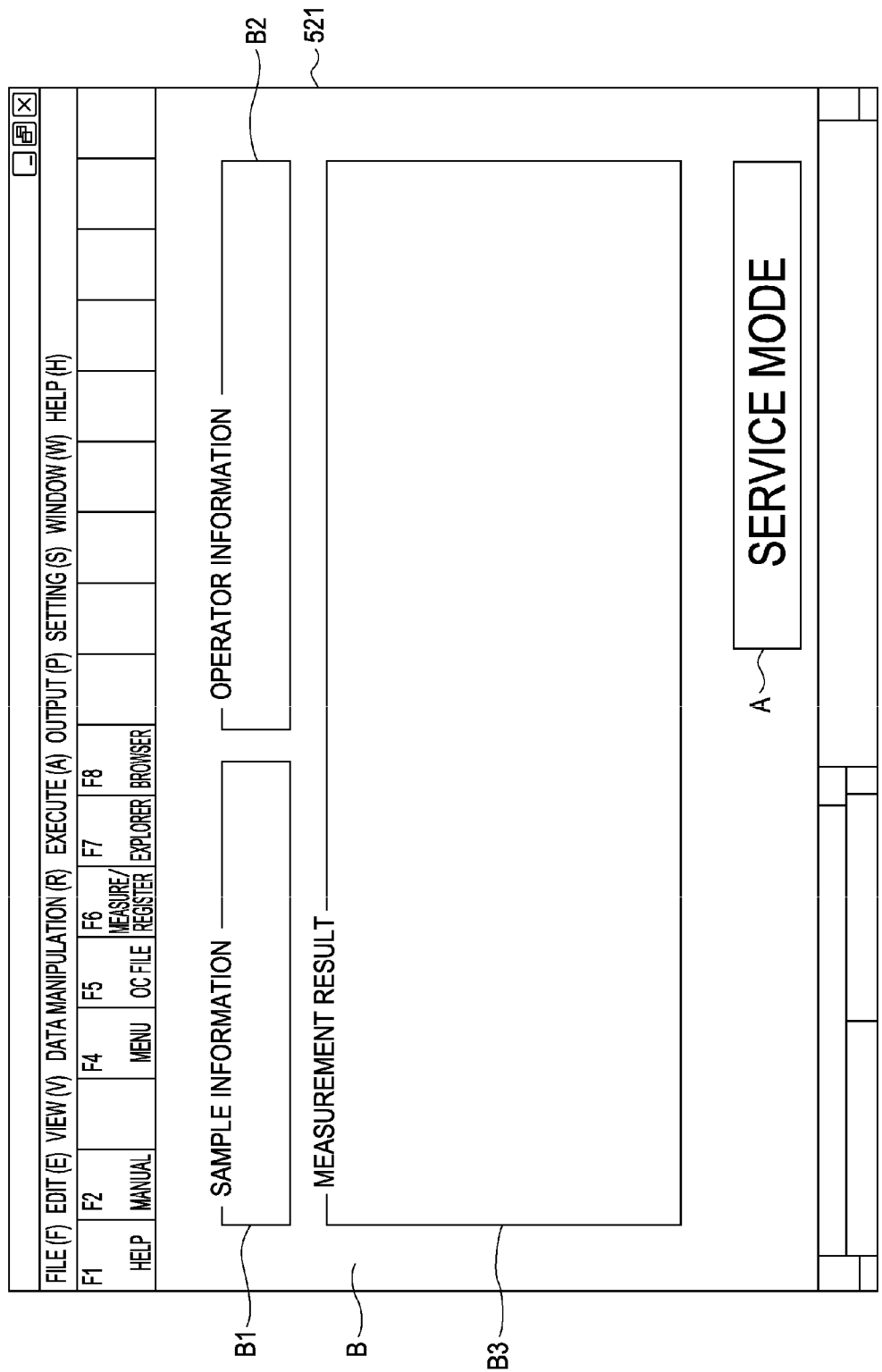
FIG. 16 is a diagram illustrating an example of a measurement result screen for serviceman according to the embodiment of the present invention.

FIG. 16 is a diagram illustrating an example of the measurement result display screen B displayed on the display section 52. A process in step S103 is mostly similar to the process in a case where the operator is a general user. However, the process differs in that the CPU 51a makes the display section 52 display thereon the measurement result display screen B illustrated in FIG. 16.

Returning to FIG. 8, when it is determined that the sample measurement command was not received (S102: NO), the CPU 51a determines whether or not the test result list screen E (see FIG. 17) is currently displayed on the display section 52 (S104). When it is determined that the test result list screen E is not currently displayed on the display section 52 (S104: NO), the CPU 51a determines whether or not a command to display the test result list screen E was received (S105). When it is determined that the command to display the test result list screen E was received (S105: YES), the CPU 51a makes the display section 52 display the test result list screen E thereon (S106).

Figure 17:
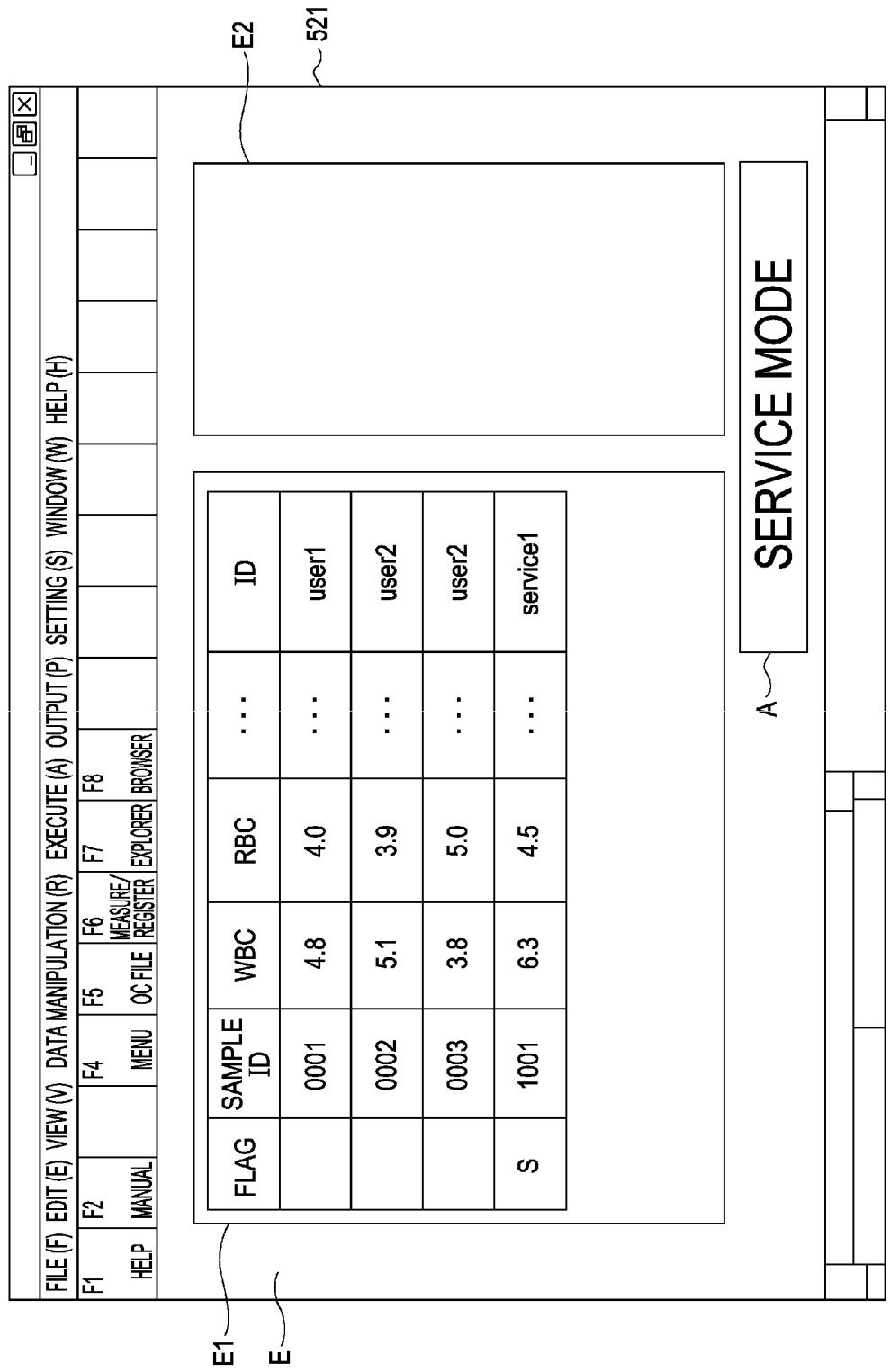
FIG. 17 is a diagram illustrating an example of a test result list screen for serviceman according to the embodiment of the present invention.

FIG. 17 is a diagram illustrating an example of the test result list screen E displayed on the display section 52. In a case where the logged-in operator is a serviceman, the CPU 51a displays in a list the test results associated with the general user's ID and the test results associated with the serviceman's ID in the summary display field E1. In this case, a character S is displayed in flag columns of the test results associated with the serviceman's ID. In this manner, the operator can identify which of the test results is obtained by the serviceman.

Returning to FIG. 8, when the test result list screen E is currently displayed on the display section 52 (S104: YES) or the CPU 51a newly commands to display the test result list screen E on the display section 52, the CPU 51a performs the process in step S102.

When it is determined that the command to display the test result list screen E was not received (S105: NO), the CPU 51a determines whether or not the operation history list screen G (see FIG. 18) is currently displayed on the display section 52 (S107). When it is determined that the operation history list screen G is not currently displayed on the display section 52 (S107: NO), the CPU 51a determines whether or not a command to display the operation history list screen G was received (S108). When it is determined that the command to display the operation history screen G was received (S108: YES), the CPU 51a makes the display section 52 display the operation history list screen G thereon (S109).

Figure 18:
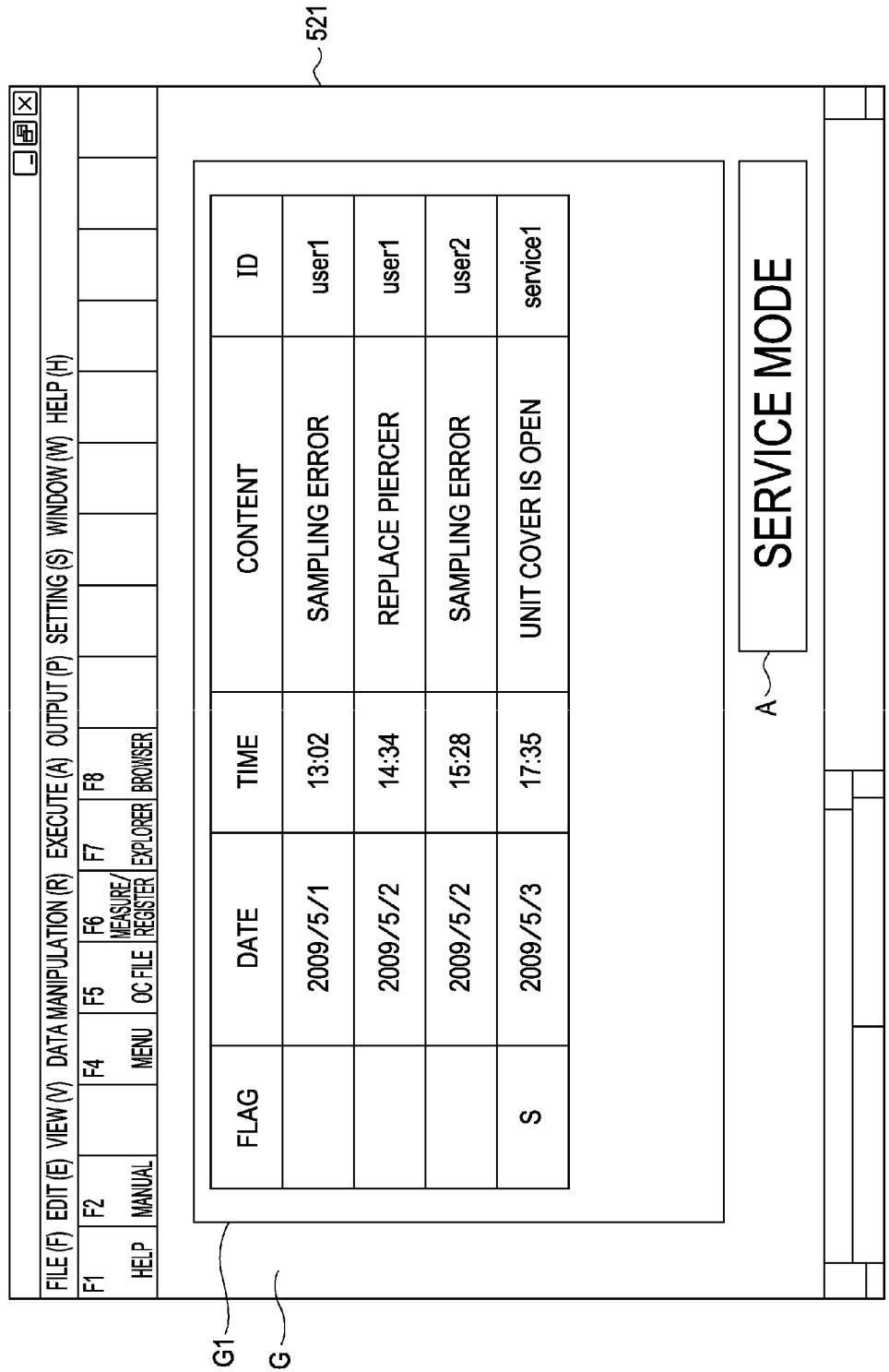
FIG. 18 is a diagram illustrating an example of an operation history list screen for serviceman according to the embodiment of the present invention.

FIG. 18 is a diagram illustrating an example of the operation history list screen G displayed on the display section 52. In a case where the logged-in operator is a serviceman, the CPU 51a displays in a list the operation histories associated with the general user's ID and the operation histories associated with the serviceman's ID in the summary display field E1. In this case, the character S is displayed in the flag columns of the operation histories associated with the serviceman's ID. In this manner, the operator can identify which of the operation histories is obtained by the serviceman.

Returning to FIG. 8, when it is determined that the command to display the operation history list screen G was not received (S108: NO), the CPU 51a determines whether or not the logoff command was received (S110). The CPU 51a performs the logoff process (S111) when it is determined that the logoff command was received (S110: YES), while the CPU 51a performs the process in step S102 when it is determined that the logoff command was not received (S110: NO).

In the hemocyte analyzer 1 according to the present embodiment, as described above, the test results and operation histories associated with the serviceman's ID are not displayed on the display section 52 when the general user is logged in. Therefore, in the hemocyte analyzer 1 according to the present embodiment, even if the serviceman does not delete the analysis results generated by the maintenance work, the general user does not need to access unnecessary information such as the generated test results and the operation histories.

In the hemocyte analyzer 1 according to the present embodiment, as described above, the character S is displayed in the flag columns of the test results and operation histories associated with the serviceman's ID when the serviceman is logged in. Therefore, in the hemocyte analyzer 1 according to the present embodiment, the serviceman can readily discriminate the test results and the operation histories associated with the general user's ID from the test results and the operation histories associated with the serviceman's ID.

Other Embodiments

The embodiments disclosed herein are illustrative and should not be construed as being restrictive in all aspects.

In the above embodiment, the hemocyte analyzer was described as an example of the sample testing apparatus. However, the present invention is not limited thereto. Examples of the sample testing apparatus may include: a blood coagulation measuring apparatus, a hemogram analyzer, an urine cell analyzer, a biochemical analyzer, and an immunity analyzer.

In the above embodiment, the conveying device 4 conveys the sample containers 100 held in the rack 101 to the sample setting part 355a. However, the present invention is not limited thereto. For example, the sample containers 100 may be directly placed in the sample setting part 355a by the operator.

In the above embodiment, the test results and the operation histories are associated with the operator's identification information (ID) and then respectively stored in the test result database 54c and the operation history database 54d. However, the present invention is not limited thereto. For example, the test results and the operation histories may be associated with at least one of the operator's identification information (ID) and information indicating the group which the operator belongs to, and may be respectively stored in the test result database 54c and the operation history database 54d.

In the above embodiment, the operator's ID and the group are associated with each other and stored in the operator information database 54b illustrated in FIG. 19, and the CPU 51a checks the operator information database 54b using the ID inputted via the input device 53 to determine whether the operator is a general user or a serviceman. However, the present invention is not limited thereto. For example, the CPU 51a may determine the operator as a general user in a case where the ID inputted via the input device 53 includes "user", and may determine the operator as a serviceman in a case where the ID inputted via the input device 53 includes "service". In this manner, the field representing groups in the operator information database 54b is no longer necessary. As a result, an area used by the operator information database 54b in the hard disc 51d can be reduced, thereby increasing an available capacity of the hard disc 51d.

In the above embodiment, the CPU 51a may automatically determine the operator as a serviceman when an ID and a password shared by a plurality of servicemen were inputted and received, and may determine the operator's attribute when the ID and password other than the shared ID and password were inputted and received by checking the operator information database 54b using the received ID. Accordingly, it becomes unnecessary to register the serviceman's ID, password and field in the operator information database 54b. As a result, an area used by the operator information database 54b in the hard disc 51d can be reduced, thereby increasing an available capacity of the hard disc 51d.

In the above embodiment, one common ID and password may be assigned to all of the servicemen while no ID and password are assigned to the general users. In this case, the CPU 51a can determine that the operator is a general user when the input of the ID and password was not received, while the CPU 51a can determine that the operator is a serviceman when the input of the common ID and password was received. In this manner, it becomes unnecessary to provide the operator information database 54b, thereby increasing an available capacity of the hard disc 51d.

In the above embodiment, all of the test results are stored in the test result database 54c. However, the present invention is not limited thereto. For example, the hard disc 51d may be provided with a test result database for general user and a test result database for serviceman, so that the CPU 51a can store the test results obtained by general users in the test result database for general user, and store the test results obtained by the serviceman in the test result database for serviceman. Then, the CPU 51a may display only the test results of the test result database for general user on the test result list screen E when the operator is a general user, and displays the test results of the test result database for general user and the test results of the test result database for serviceman on the test result list screen E when the operator is a serviceman. As a result, the management of the test results is facilitated since the test results obtained by the general user and the test results obtained by the serviceman are respectively stored in the different databases.

In the above embodiment, the operation histories of the measurement unit 3 are associated with the operator's ID and then stored in the operation history database 54d as illustrated in FIG. 21. However, the present invention is not limited thereto. For example, the hard disc 51d may be provided with an operation history database for general user and an operation history database for serviceman, so that the CPU 51a can store the operation histories obtained by general user in the operation history database for general user, and store the operation histories obtained by the serviceman in the operation history database for serviceman. Then, the CPU 51a may display only the operation histories of the operation history database for general user on the test result list screen G when the operator is a general user, and display the operation histories of the operation history database for general user and the operation histories of the operation history database for serviceman on the test result list screen G when the operator is a serviceman. As a result, the management of the operation histories is facilitated since the operation histories obtained by the general user and the operation histories obtained by the serviceman are respectively stored in the different databases.

What is claimed is:

1. An information management apparatus communicatively connected to a sample testing apparatus which tests a sample to obtain a test result, the information management apparatus comprising:
 a receiving section that receives identification information of an operator, the identification information corresponding to a first attribute indicating that the operator is a person who belongs to a facility where the sample testing apparatus is installed or a second attribute indicating that the operator is a person in charge of a maintenance work, and the identification information being inputted by the operator;
 a non-transitory memory;
 a display section; and
 a processor programmed to execute a computer program that enables the processor to:
  store in the memory one or more test results associated with the identification information received by the receiving section, the one or more test results being obtained by testing one or more samples by the sample testing apparatus by the operator;
  when the identification information received by the receiving section corresponds of the first attribute, make the display section not display a test result associated with identification information corresponding to the second attribute, but display a test result associated with identification information corresponding to the first attribute based on the one or more test results stored in the memory;
  when the identification information received by the receiving section corresponds to the second attribute, make the display section display the test result associated with identification information corresponding to the first attribute and the test result associated with identification information corresponding to the second attribute based on the one or more test results stored in the memory so that the test result associated with identification information corresponding to the first attribute can be discriminated from the test result associated with identification information corresponding to the second attribute;
  when the identification information received by the receiving section corresponds to the second attribute, prevent the operator from modifying and deleting the test result associated with the identification information corresponding to the first attribute, and
  when the identification information received by the receiving section corresponds to the first attribute, allow the operator to modify and delete the test result associated with the identification information corresponding to the first attribute.

2. The information management apparatus of claim 1, wherein the person who belongs to the facility is one of a manager or a general user, and the first attribute indicates that the operator is a general user.

3. The information management apparatus of claim 2, wherein the receiving section comprises an input device for inputting the identification information via the input device.

4. The information management apparatus of claim 1, wherein the processor is further configured to execute the program to store one or more operation histories, which are transmitted from the sample testing apparatus, so as to be associated with the identification information received by the receiving section in the memory; and the processor is further programmed to:
when the identification information received the receiving section corresponds to the second attribute, make the display section not display an operation history associated with an identification information corresponding to the second attribute, but display an operation history associated with an identification information corresponding to the first attribute based on the one or more operation histories stored in the memory when the identification information received by the receiving section corresponds to the first attribute; and
when the identification information received the receiving section corresponds to the second attribute, make the display section display the operation history associated with the identification information corresponding to the first attribute and the operation history associated with the identification information corresponding to the second attribute in the one or more operation histories stored in the memory.

5. The information management apparatus of claim 4, wherein the processor is further configured to execute the program make the display section display the operation history associated with the identification information corresponding to the first attribute and the operation history associated with the identification information corresponding to the second attribute so that the respective operation histories can be discriminated from each other when the identification information received by the receiving section corresponds to the second attribute.

6. A sample testing apparatus comprising:
a receiving section that receives identification information of an operator that is entered by the operator, the identification information corresponding to a first attribute indicating that the operator is a person who belongs to a facility where the sample testing apparatus is installed or a second attribute indicating that the operator is a person in charge of maintenance work;
a testing section that tests a sample to obtain a test result according to action taken by the operator;
a non-transitory memory;
a display section; and
a controller configured to execute a computer program that enables the controller to:
store in the memory one or more test results associated with the identification information received by the receiving section, the one or more test results being obtained by testing one or more samples by the testing section;
when the identification information received by the receiving section corresponds to the first attribute, make the display section not display a test result associated with an identification information corresponding to the second attribute, but display a test result associated with an identification information corresponding to the first attribute based on the one or more test results stored in the memory;
when the identification information received by the receiving section corresponds to the second attribute, make the display section display the test result associated with the identification information corresponding to the first attribute and the test result associated with the identification information corresponding to the second attribute based on the one or more test results stored in the memory, so that the test result associated with identification information corresponding to the first attribute is discriminated from the test result associated with identification information corresponding to the second attribute;
when the identification information received by the receiving section corresponds to the second attribute, prevent the operator from modifying and the deleting the test result associated with the identification information corresponding to the first attribute, and
when the identification information received by the receiving section corresponds to the first attribute, allow the operator to modify and delete the test result associated with the identification information corresponding to the first attribute.

7. The sample testing apparatus of claim 6, wherein the person who belongs to the facility is one of a manager or a general user, and the first attribute indicates that the operator is a general user.

8. The sample testing apparatus of claim 7, wherein when the identification information received by the receiving section corresponds to the second attribute, the controller is further configured to execute the program to permit the operator to execute a function which is not allowed for an operator with identification information that corresponds to the first attribute.

9. The sample testing apparatus of claim 6, wherein the controller is further configured to execute the program to store the identification information corresponding to the first attribute or the second attribute in the memory; and
the controller is further configured to execute the program to determine whether the identification information received by the receiving section corresponds to the first attribute or the second attribute based on the identification information that is stored in the memory.

10. The sample testing apparatus of claim 6, wherein the receiving section comprises an input device, and the controller is further configured to execute the program to determine that the identification information of the operator corresponds to the first attribute when a string of characters inputted via the input device as the identification information of the operator includes a first string of characters indicating the first attribute, and the processor is further programmed to determine that the identification information corresponds to the second attribute when the string of characters includes a second string of characters indicating the second attribute.

11. The sample testing apparatus of claim 6, wherein the controller is further configured to execute the program to store one or more operation histories of the testing section associated with the identification information received by the receiving section in the memory; and
when the identification information received by the receiving section corresponds to the first attribute, the controller is further configured to execute the program to make the display section not display an operation history associated with the identification information corresponding to the second attribute, but display an operation history associated with the identification information corresponding to the first attribute based on the one or more operation histories stored in the memory; and
when the identification information received by the receiving section corresponds to the second attribute, make the display section display the operation history associated with the identification information corresponding to the first attribute and the operation history associated with the identification information corresponding to the second attribute based on the one or more operation histories stored in the memory.

12. The sample testing apparatus of claim 11, wherein the receiving section comprises an input device for inputting the identification information via the input device; and the controller is further configured to execute the program to make the display section display the operation history associated with the identification information corresponding to the first attribute and the operation history associated with the identification information corresponding to the second attribute so that the respective operation histories are discriminated from each other when the identification information entered via the input device corresponds to the second attribute.

13. The sample testing apparatus of claim 6, wherein the memory includes a first database and a second database, and when the identification information received by the receiving section corresponds to the first attribute, the controller is further configured to execute the program to store the test result obtained by testing the sample by the testing section in the first database;

when the identification information received by the receiving section corresponds to the second attribute, the controller is further configured to execute the program to store the test result obtained by testing the sample by the testing section in the second database;

when the identification information received by the receiving section corresponds to the first attribute, the controller is further configured to execute the program to make the display section not display the test result stored in the second database, but display the test result stored in the first database; and when the identification information received by the receiving section corresponds to the second attribute, the controller is further configured to execute the program to make the display section display the test result stored in the first database and the test result stored in the second database.

14. The sample testing apparatus of claim 13, wherein when the identification information received by the receiving section corresponds to the first attribute, the controller is further configured to execute the program to store an operation history obtained by the testing section in the first database;

when the identification information received by the receiving section corresponds to the second attribute, the controller is further configured to execute the program to, store an operation history obtained by the testing section in the second database;

when the identification information received by the receiving section corresponds to the first attribute, the controller is further configured to execute the program to, make the display section not display the operation history stored in the second database but display the operation history stored in the first database; and when the identification information received by the receiving section corresponds to the second attribute, the controller is further configured to execute the program to, make the display section display the operation history stored in the first database and the operation history stored in the second database.

15. A sample testing apparatus comprising: a receiving section that receives identification information of an operator, the identification information corresponding to a first attribute indicating that the operator is a person who belongs to a facility where the sample testing apparatus is installed or a second attribute indicating that the operator is a person in charge of a maintenance work, and the identification information being inputted by the operator;

a testing section which tests a sample to obtain a test result;
a non-transitory memory;
a display section; and
a controller configured to execute a computer program that enables the controller to:

store in the memory one or more first test results obtained by testing one or more samples from one or more test subjects, each of the one or more first test results being associated with identification information corresponding to the first attribute;

store in the memory one or more second test results obtained by testing one or more controls specimens, each of the one or more second test results being associated with identification information corresponding to the second attribute;

when the identification information received by the receiving section corresponds to the first attribute, make the display not display the one or more second test results, but display the one or more first test results stored in the memory;

when the identification information received by the receiving section corresponds to the second attribute, make the display section display the one or more first test results and the one or more second test results so that the one or more first test results associated with identification information corresponding to the first attribute can be discriminated from the one or more second test results associated with identification information corresponding to the second attribute;

when the identification information received by the receiving section corresponds to the second attribute, prevent the operator from modifying and deleting the one or more first test results associated with the identification information corresponding to the first attribute, and when the identification information received by the receiving section corresponds to the first attribute, allow the operator to modify and delete the one or more first test results associated with the identification information corresponding to the first attribute.

* * * * *